United States Patent [19]
Bencherif et al.

[11] Patent Number: 5,583,140
[45] Date of Patent: Dec. 10, 1996

[54] PHARMACEUTICAL COMPOSITIONS FOR THE TREATMENT OF CENTRAL NERVOUS SYSTEM DISORDERS

[76] Inventors: Merouane Bencherif, 5437-B Countryside Dr., Winston-Salem, N.C. 27105; William S. Caldwell, 1270 Yorkshire Rd., Winston-Salem, N.C. 27106; Gary M. Dull, 1175 Sequoia Dr.; Patrick M. Lippiello, 1233 Arboretum Dr., both of Lewisville, N.C. 27023

[21] Appl. No.: 437,153

[22] Filed: May 17, 1995

[51] Int. Cl.$^6$ .................... A61K 31/44; A61K 31/505
[52] U.S. Cl. ............................. 514/299; 514/256
[58] Field of Search ..................... 514/299, 256

[56] References Cited

U.S. PATENT DOCUMENTS

| | | | |
|---|---|---|---|
| 3,870,794 | 3/1975 | Hutchinson et al. | 424/264 |
| 4,342,762 | 8/1982 | Budai et al. | 424/246 |
| 4,578,394 | 3/1986 | Allen et al. | 514/332 |
| 4,680,172 | 7/1987 | Leeson | 424/449 |
| 4,786,646 | 11/1988 | Guthrie et al. | 514/346 |
| 4,916,145 | 4/1990 | Tilley et al. | 514/357 |
| 4,927,838 | 5/1990 | Guthrie et al. | 514/337 |
| 4,965,074 | 10/1990 | Leeson | 424/449 |
| 5,110,933 | 5/1992 | Berlin et al. | 546/114 |
| 5,210,076 | 5/1993 | Berliner et al. | 514/21 |
| 5,212,188 | 5/1993 | Caldwell et al. | 514/343 |
| 5,219,872 | 6/1993 | Galliani et al. | 514/357 |
| 5,219,873 | 6/1993 | Galliani et al. | 514/357 |
| 5,225,567 | 7/1993 | Moon et al. | 548/518 |
| 5,227,391 | 7/1993 | Caldwell et al. | 514/343 |
| 5,242,935 | 9/1993 | Lippiello et al. | 514/343 |
| 5,262,427 | 11/1993 | Nielson et al. | 514/304 |
| 5,346,906 | 9/1994 | Baker et al. | 514/305 |

FOREIGN PATENT DOCUMENTS

| | | |
|---|---|---|
| 0377520 | 7/1990 | European Pat. Off. . |
| 92/21339 | 12/1992 | WIPO . |

OTHER PUBLICATIONS

Kelly, T. et al., "Maxonine: Structure Correction and Synthesis", *Tetrahedron Letters*, vol. 34, No. 39, pp. 6173–6176 (1993).
Leete, E. et al. "Formation of 5–Fluoronicotine from 5–Fluoronicotinic Acid in Nicotiana Tabacum*", *Phytochemistry*, 1971, vol. 10, pp. 2687 to 2692.
Lynch, B. et al. "Pyrazolo [3,4–b]pyridines: Syntheses, reactions, and nuclear magnetic resonance spectra", *Can. J. Chem.* 66, 420 (1988).
Rubtsov M. et al., Translated from *Zhurnal Obshchei Khimii*, "Hofmann Cleavage of 6,9–diazoniadispiro–[5.2.5.2]hexadecane dichloride with methanolic potassium hydroxide", vol. 35, No. 4, pp. 621–628 (Apr. 1965).
Sadikov, A. et al., Translated from *Zhurnal Obshchei Khimii*, "Syntheses Based on Anabasine", vol. 33, No. 10, pp. 3417–3420 (Oct. 1963).

Seeman, J. et al., *Anal. Chem.*, "Enantiomeric Resolution and Chiral Recognition of Racemic Nicotine and Nicotine Analogues by β–Cyclodextrin Complexation. Structure–Enantiomeric Resolution Relationships in Host–Guest Interactions", 60, 2120–2127 (1988).
Baron, J., "Cigarette smoking and Parkinson's disease", *Neurology*, vol. 36, pp. 1490–1496 (1986).
Benwell, M. et al., "Evidence that Tobacco Smoking Increases the Density of (–)–[$^3$H] Nicotine Binding Sites in Human Brain", *Journal of Neurochemistry*, vol. 50, pp. 1243–1247 (1988).
Clark, P. et al., "Electrophysiological actions of nicotine on substantia nigra single units", *Br. J. Pharm.*, vol. 85, pp. 827–835 (1985).
Decina, P. et al., "Cigarette Smoking and Neuroleptic–Induced Parkinsonism", *Biol. Psychiatry*, vol. 28, pp. 502–508 (1990).
Giacobini, E., "Pharmacotherapy of Alzheimer's Disease: New Drugs and Novel Strategies", *Alzheimer's Disease: Advances in Clinical and Basic Research*, S61, pp. 529–538 (1993).
Giacobini, E., "New Cholinesterase Inhibitors for Treatment of Alzheimer's Disease", *Alzheimer's Disease: Basic Mechanisms, Diagnosis and Therapeutic Strategies*, S80, pp. 627–631 (1991).
Giacobini, E., "Cholinergic Receptors in Human Brain: Effects of Aging and Alzheimer's Disease", *Journal of Neuroscience Research*, vol. 27, pp. 548–560 (1990).
Giacobini, E., "The Second Generation of Cholinesterasse Inhibitors: Pharmacological Aspects", *Pharmacological Basis of Cholinergic Therapy of Alz. Dis.*, Eds., Becker, R. et al. Boxton:Birkhauser (1991).
Giacobini, E. et al., "Toward a Third Generation of Cholinesterase Inhibitors", *Pharmacological Basis of Cholinergic Therapy of Alz. Dis.*, Eds., Becker, R. et al., Boxton:Birkhauser, (1991).
Hall, G. et al., "Effects of Nicotine on the Release of $^3$H–Noradrenaline from the Hypothalamus", *Biochemical Pharmacology*, vol. 21, pp. 1829–1838 (1972).
Harsing, L. et al., "Dopamine Efflux from Striatum After Chronic Nicotine: Evidence for Autoreceptor Desensitization", *Journal of Neurochemistry*, vol. 59, pp. 48–54 (1993).
Hery, F. et al., "Control of the Release of Newly Synthetized $^3$H–5–Hydroxytryptamine by Nicotinic and Muscarinic Receptors in Rat hypothalamic Slices", *Arch. Int. Pharmacodyn. Ther.*, vol. 296, pp. 91–97 (1977).

(List continued on next page.)

*Primary Examiner*—Marianne M. Cintins
*Assistant Examiner*—William R. A. Jarvis

[57] ABSTRACT

Patients susceptible to or suffering from central nervous system disorders (e.g., neurodegenerative diseases including presenile dementia, senile dementia of the Alzheimer's type, and Parkinsonism including Parkinson's disease, and other CNS disorders including attention deficit disorder, schizophrenia and Tourette's syndrome) are treated by administering an effective amount of 2-azabicyclo[2.2.1]hept-5-ene and 2-azabicyclo[2.2.2]oct-5-ene compounds.

15 Claims, No Drawings

OTHER PUBLICATIONS

Janson, A. et al., "Protective effects of chronic nicotine treatment on lesioned nigrostriatal dopa neurons in the male rat", *Progress in Brain Research*, vol. 79, pp. 257–265 (1989).

Jarvik, M. "Beneficial effects of nicotine", *British Journal of Addiction*, vol. 86, pp. 571–575 (1991).

Jones, A. et al., "Alzheimer's Disease: Clinical and Pathological Characteristics", *Intern. J. Neuroscience*, vol. 50, pp. 147–168 (1990).

Marks, M. et al., "Effects of Chronic Nicotine Infusion on Tolerance Development and Nicotinic Receptors", *The Journal of Pharmacology and Experimental Therapeutics*, vol. 226, pp. 817–825 (1983).

Hughes, "Proceedings from Intl. Symp. Nic.", S40 (1994).

New house, P. et al., "Intravenous nicotine in Alzheimer's disease: a pilot study", *Psychopharmacology*, vol. 95, pp. 171–175 (1988).

Nordberg, A. et al., "The role of nicotinic receptors in the pathophysiology of Alzheimer's disease", *Progress in Brain Research*, vol. 79, pp. 353–362 (1989).

Onaivi, E. et al., "Chronic Nicotine Reverses Age–Associated Increases in Tail–Flick Latency and Anxiety in Rats", *Life Sciences*, vol. 54, pp. 193–202 (1994).

Perry E., "The Cholinergic Hypothesis–Ten Years On", *British Medical Bulletin*, vol. 42, pp. 63–69 (1986).

Pomponi, M. et al., "Present state and future development of the therapy of Alzheimer disease", *Aging*, vol. 2(2), pp. 125–153 (1990).

Rapier, C. et al., "Stereoselective Nicotine–Induced Release of Dopamine from Striatal Synaptosomes: Concentration Dependence and Repetitive Stimulation", *Journal of Neurochemistry*, vol. 50, pp. 1123–1130 (1988).

Rinne, J. et al., "A postmortem study of brain nicotinic receptors in Parkinson's and Alzheimer's disease", *Brain Research*, vol. 547, pp. 167–170 (1991).

Rowell, P., "Current Concepts on the Effects of Nicotine on Neurotransmitter Release in the Central Nervous System", *Adv. Behav. Biol.*, vol. 31, pp. 191–208 (1987).

Rowell, P. et al., "Nicotinic Stimulation of [$^3$H]Acetylcholine Release from Mouse Cerebral Cortical Synaptosomes", *Journal of Neurochemistry*, vol. 43, pp. 1593–1598 (1984).

Sahakian, B. et al., "The Effects of Nicotine on Attention, Information Processing, and Short–Term Memory in Patients ith Dementia of the Alzheimer Type", *British Journal of Psychiatry*, vol. 154, pp. 797–800 (1989).

Sanberg, P. et al., "Nicotine Potentiation of Haloperidol–Induced Catalepsy: Striatal Mechanisms", *Pharmacology Biochemistry and Behavior*, vol. 46, pp. 303–307 (1993).

Sandor, N. et al., "Effect of nicotine on dopaminergic–cholinergic interaction in the striatum", *Brain Research*, vol. 567, pp. 313–316 (1991).

Sherwood, *Human Psychopharm.*, vol. 8, pp. 155–184 (1993).

Sjak–Shie, N. et al., "Effects of chronic nicotine and pilocarpine administration on neocortical neuronal density and [$^3$H] GABA uptake in nucleus basalis lesioned rats", *Brain Research*, vol. 624, pp. 295–298 (1993).

Smith, C. et al., "Nicotine, Parkinson's and Alzheimer's Disease", *Rev. in Neuroscience*, vol. 3, pp. 25–43 (1992).

Toth, E. et al., "Effect of Nicotine on Extracellular Levels of Neurotransmitters Assessed by Microdialysis in Various Brain Regions: Role of Glutamic Acid", *Neurochemical Research*, vol. 17(3), pp. 265–271 (1992).

van Duijan, C. et al., "Relation between nicotine intake and Alzheimer's disease", *BMJ*, vol. 302, pp. 1491–1494 (1991).

Vizi, E., "Acetylcholine release from guinea–pig ileum by parasympathetic ganglion stimulants and gastrin–like polypeptides", *British Journal Pharmacology*, vol. 47, pp. 765–777 (1973).

Physicians' Desk Reference, 48 Edition, pp. 899–903 (1994), "Sinemet".

Physicians' Desk Reference, 48 Edition, pp. 2067–2069 (1994), "Parlodel".

Physicians' Desk Reference, 48 Edition, pp. 2309–2311 (1994), "Eldepryl".

Hodges, H. et al., "Nicotine as a Tool to Characterize the Role of the Forebrain Cholinergic Pr System in Cognition", *Biology of Nicotine*, pp. 157–182 (1991).

Pomerleau, et al., "The Effects of Cigarette Smoking on Pain and Anxiety", *Addictive Behavior* 9, pp. 265–271 (1984).

Wagner, et al., "Does Smoking Reduce the Risk of Neuroleptic Parkinsonoids?", *Pharmacopsychiatry*, vol. 21, pp. 302–303 (1988).

Baron, J., "Proceedings from Intl. Symp. Nic.", S42 (1994).

Janson, A. et al., "Proceedings from Intl. Symp. Nic.", S43 (1994).

Levin, E. et al., "Proceedings from Intl. Symp. Nic.", S44 (1994).

Joseph M. et al., "Proceedings from Intl. Symp. Nic.", S45 (1994).

Newhouse, P. et al., "Proceedings from Intl. Symp. Nic.", S46 (1994).

Adler, L. et al., "Normalization by Nicotine of Deficient Auditory Sensory Gating in the Relatives Schizophrenics", *Biol. Psychiatry*, vol. 32, pp. 607–616 (1992).

Calderon–Gonzalez R., "Tourette Syndrome", *Intern. Pediat.*, vol. 8(2), pp. 176–188 (1993).

Devor, E. et al., "Nicotine and Tourette's Syndrome", *The Lancet*, vol. 8670, p. 1046 (1989).

Faraone, S. et al., "An Exploratory Study of ADHD among Second–Degree Relatives of ADHD Children", *Biol. Psychiatry*, vol. 35(6), pp. 398–402 (1994).

Glassman, A., "Cigarette Smoking: Implications for Psychiatric Illness", *Am J. Psychiatry*, vol. 1 546–553 (1993).

Lieberman, J. et al., "Neurochemistry and Neuroendocrinology of Schizophrenia: A Selective Review", *Schizophr. Bull.*, vol. 19, pp. 371–429 (1993).

Malone, M. et al., "Hemispheric Processing and Methylphenidate Effects in Attention–Deficit Hyperactivity Disorder", *J. Child Neurol.*, vol. 9(2), pp. 181–189 (1994).

McConville, B. et al., "Nicotine Potentiation of Haloperidol in Reducing Tic Frequency in Tourette's Disorder", *Am. J. Psychiatry*, vol. 148, pp. 793–794 (1991).

McConville, B. et al., "The Effects of Nicotine Plus Haloperidol Compared to Nicotine Only and Placebo Nicotine Only in Reducing Tic Severity and Frequency in Tourette's Disorder", *Biol. Psychiatry*, vol. 31, pp. 832–840 (1992).

Newhouse, P. et al., "The role of nicotine and nicotine mechanisms in neuropsychiatric disease", *British Journal of Addiction*, vol. 86, pp. 521–526 (1991).

Sitaram, N. et al., "Human Serial Learning: Enhancement with Arecholine and Choline and Impairment with Scopolamine", *Science*, vol. 201, pp. 274–276 (1978).

Physician's Desk Reference, 48 Edition, pp. 410–411 (1994), "Cylert".

Physicians's Desk Reference, 48 Edition, pp. 520–523 (1994), "Prolixin".

Physician's Desk Reference, 48 Edition, pp. 612–614 (1994), "Catapres".

Physician's Desk Reference, 48 Edition, pp. 835–836 (1994), "Ritalin".

Physician's Desk Reference, 48 Edition, pp. 977–979 (1994), "Orap".

Physician's Desk Reference, 48 Edition, pp. 1357–1359 (1994), "Haldol".

Physican's Desk Reference, 48 Edition, pp. 1935–1936 (1994), "Klonopin".

Physician's Desk Reference, 48 Edition, pp. 2248–2250 (1994), "Dexedrine".

Hechtman, L., "Genetic and Neurobiological Aspects of Attention Deficit Hyperactive Disorder: A Review", *J. Psychiatry Neurosci.*, vol. 19(3), pp. 193–201 (1994).

Merriam, et al., "Schizophrenia as a Neurobehavioral Disorder", *Psychiatr. Annals.*, vol. 23, p. 178 (1993).

Sanberg, et al., *Proceedings from Intl. Symp. Nic.*, S39 (1994).

Vinson, D., "Therapy for Attention–Deficit Hyperactivity Disorder", *Arch. Fam. Med.*, vol. 3(5), p. 451 (1994).

Warburton, et al., "Cholinergic control of cognitive resources", *Neuropsychobiology*, Eds., Mendl et al., pp. 43–46 (1993).

Freedman, R. et al., *Proceedings from Intl. Symp. Nic.*, S41 (1994).

Acheson, R. et al., *J. Chem. Soc. Perkin Trans.*, vol. 2, pp. 579–585 (1980).

Erdtman, H. et al., *Acta Chem. Scand.*, vol. 17, pp. 1717–1726 (1963).

Frank, W. et al., *J. Org. Chem.*, vol. 43(15), pp. 2947–2949 (1978).

Gol'dfarb, Y. et al., *J. Gen. Chem.*, USSR(Engl. Transl.), vol. 39, pp. 1071–1075 (1969).

Kamimura, H. et al., *Agr. Biol. Chem.*, vol. 27, No. 10, pp. 684–688 (1963).

LaForge, F., *JACS*, vol. 50, pp. 2477–2483 (1928).

Loffler, K. et al., *Chem. Ber.*, vol. 42, pp. 3431–3428 (1909).

Malek, N. et al., *J. Org. Chem.*, vol. 47, pp. 5395–5397 (1982).

Pinner, A., *Chem. Ber.*, pp. 2861–2870 (1894).

Rondahl, L., *Acta Pharm. Suec.*, vol. 14, No. 2, pp. 113–118 (1977).

Rondahl, L., *Acta Pharm. Suec.*, vol. 13, pp. 229–234 (1976).

Sprouse, C. et al., Abstracts of Papers, p. 32, Coresta/TCRC, Joint Conference (1972).

Ashimori, A. et al., *Chem. Pharm. Bull.* vol. 38(9), pp. 2446–2458 (1990).

Hamon, *Trends in Pharmacol. Res.*, vol. 15, pp. 36–39 (1994).

PHARMACEUTICAL COMPOSITIONS FOR THE TREATMENT OF CENTRAL NERVOUS SYSTEM DISORDERS

BACKGROUND OF THE INVENTION

The present invention relates to compounds having pharmaceutical properties, and in particular, to compounds useful for preventing and treating central nervous system (CNS) disorders. The present invention relates to a method for treating patients suffering from or susceptible to such disorders, and in particular, to a method for treating patients suffering from those disorders which are associated with neurotransmitter system dysfunction. The present invention also relates to compositions of matter useful as pharmaceutical compositions in the prevention and treatment of CNS disorders which have been attributed to neurotransmitter system dysfunction.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses; and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a cholinergic deficiency, a dopaminergic deficiency, an adrenergic deficiency and/or a serotonergic deficiency. CNS disorders of relatively common occurrence include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

Senile dementia of the Alzheimer's type (SDAT) is a debilitating neurodegenerative disease, mainly afflicting the elderly; characterized by a progressive intellectual and personality decline, as well as a loss of memory, perception, reasoning, orientation and judgment. One feature of the disease is an observed decline in the function of cholinergic systems, and specifically, a severe depletion of cholinergic neurons (i.e., neurons that release acetylcholine, which is believed to be a neurotransmitter involved in learning and memory mechanisms). See, Jones, et al., *Intern. J. Neurosci.*, Vol. 50, p. 147 (1990); Perry, *Br. Med. Bull.*, Vol. 42, p. 63 (1986) and Sitaram, et al., *Science*, Vol. 201, p. 274 (1978). It has been observed that nicotinic acetylcholine receptors, which bind nicotine and other nicotinic agonists with high affinity, are depleted during the progression of SDAT. See Giacobini, *J. Neurosci. Res.*, Vol. 27, p. 548 (1990); and Baron, *Neurology*, Vol. 36, p. 1490 (1986). As such, it would seem desirable to provide therapeutic compounds which either directly activate nicotinic receptors in place of acetylcholine or act to minimize the loss of those nicotinic receptors.

Certain attempts have been made to treat SDAT. For example, nicotine has been suggested to possess an ability to activate nicotinic cholinergic receptors upon acute administration, and to elicit an increase in the number of such receptors upon chronic administration to animals. See, Rowell, *Adv. Behav. Biol.*, Vol. 31, p. 191 (1987); and Marks, *J. Pharmacol. Exp. Ther.*, Vol. 226, p. 817 (1983). It also has been proposed that nicotine can act directly to elicit the release of acetylcholine in brain tissue, to improve cognitive functions, and to enhance attention. See, Rowell, et al., *J. Neurochem.*, Vol. 43, p. 1593 (1984); Sherwood, *Human Psychopharm.*, Vol. 8, pp. 155–184 (1993); Hodges, et al., *Bio. of Nic.*, Edit. by Lippiello, et al., p. 157 (1991); Sahakian, et al., *Br. J. Psych.*, Vol. 154, p. 797 (1989); and U.S. Pat. Nos. 4,965,074 to Leeson and 5,242,935 to Lippiello et al. Other methods for treating SDAT have been proposed, including U.S. Pat. Nos. 5,212,188 to Caldwell et al. and 5,227,391 to Caldwell et al. and European Patent Application No. 588,917. Another proposed treatment for SDAT is Cognex, which is a capsule containing tacrine hydrochloride, available from Parke-Davis Division of Warner-Lambert Company, which reportedly preserves existing acetylcholine levels in patients treated therewith.

Parkinson's disease (PD) is a debilitating neurodegenerative disease, presently of unknown etiology, characterized by tremors and muscular rigidity. A feature of the disease appears to involve the degeneration of dopaminergic neurons (i.e., which secrete dopamine). One symptom of the disease has been observed to be a concomitant loss of nicotinic receptors which are associated with such dopaminergic neurons, and which are believed to modulate the process of dopamine secretion. See, Rinne, et al., *Brain Res.*, Vol. 54, pp. 167–170 (1991) and Clark, et al., *Br. J. Pharm.*, Vol. 85, pp. 827–835 (1985). It also has been proposed that nicotine can ameliorate the symptoms of PD. See, Smith et al., *Rev. Neurosci.*, Vol. 3(1), pp. 25–43 (1982).

Certain attempts have been made to treat PD. One proposed treatment for PD is Sinemet CR, which is a sustained-release tablet containing a mixture of carbidopa and levodopa, available from The DuPont Merck Pharmaceutical Co. Another proposed treatment for PD is Eldepryl, which is a tablet containing selefiline hydrochloride, available from Somerset Pharmaceuticals, Inc. Another proposed treatment for PD is Parlodel, which is a tablet containing bromocriptine mesylate, available from Sandoz Pharmaceuticals Corporation. Another method for treating PD and a variety of other neurodegenerative diseases has been proposed in U.S. Pat. No. 5,210,076 to Berliner et al.

Tourette's syndrome (TS) is an autosomal dominant neuropsychiatric disorder characterized by a range of neurological and behavioral symptoms. Typical symptoms include (i) the onset of the disorder before the age of 21 years, (ii) multiple motor and phonic tics although not necessarily concurrently, (iii) variance in the clinical phenomenology of the tics, and (iv) occurrence of quasi daily tics throughout a period of time exceeding a year. Motor tics generally include eye blinking, head jerking, shoulder shrugging and facial grimacing; while phonic or vocal tics include throat clearing, sniffling, yelping, tongue clicking and uttering words out of context. The pathophysiology of TS presently is unknown, however it is believed that neurotransmission dysfunction is implicated with the disorder. See, Calderon-Gonzalez et al., *Intern. Pediat.*, Vol. 8(2), pp. 176–188 (1993) and *Oxford Textbook of Medicine*, Eds. Weatherall et al., Chapter 21.218 (1987).

It has been proposed that nicotine pharmacology is beneficial in suppressing the symptoms associated with TS. See, Devor et al., *The Lancet*, Vol. 8670, p. 1046 (1989); Jarvik, *British J. of Addiction*, Vol. 86, pp. 571–575 (1991); McConville et al., *Am. J. Psychiatry.*, Vol. 148 (6), pp. 793–794 (1991); Newhouse et al., *Brit. J, Addic.*, Vol. 86, pp. 521–526 (1991); McConville et al., *Biol. Psychiatry*, Vol.

31, pp. 832–840 (1992); and Sanberg et al., *Proceedings from Intl. Syrup. Nic.*, S39 (1994). It also has been proposed to treat TS using Haldol, which is haloperidol available from McNeil Pharmaceutical; Catapres, which is clonidine available from Boehringer Ingelheim Pharmaceuticals, Inc., Orap, which is pimozide available from Gate Pharmaceuticals; Prolixin, which is fluphenazine available from Apothecon Division of Bristol-Myers Squibb Co.; and Klonopin, which is clonazepam available from Hoffmann-LaRoche Inc.

Attention deficit disorder (ADD) is a disorder which affects mainly children, although ADD can affect adolescents and adults. See, Vinson, *Arch. Fam. Med.*, Vol. 3(5), pp. 445–451 (1994); Hechtman, *J. Psychiatry Neurosci.*, Vol. 19 (3), pp. 193–201 (1994); Faraone et al., *Biol. Psychiatry.*, Vol. 35(6), pp. 398–402 (1994) and Malone et al., *J. Child Neurol.*, Vol. 9(2), pp. 181–189 (1994). Subjects suffering from the disorder typically have difficulty concentrating, listening, learning and completing tasks; and are restless, fidgety, impulsive and easily distracted. Attention deficit disorder with hyperactivity (ADHD) includes the symptoms of ADD as well as a high level of activity (e.g., restlessness and movement). Attempts to treat ADD have involved administration of Dexedrine, which is a sustained release capsule containing dextroamphetamine sulfate, available from SmithKline Beecham Pharmaceuticals; Ritalin, which is a tablet containing methylphenidate hydrochloride, available from Ciba Pharmaceutical Company; and Cylert, which is a tablet containing premoline, available from Abbott Laboratories. In addition, it has been reported that administration of nicotine to an individual improves that individual's selective and sustained attention. See, Warburton et al., *Cholinergic control of cognitive resources, Neuropsychobiology*, Eds. Mendlewicz, et al., pp 43–46 (1993).

Schizophrenia is characterized by psychotic symptoms including delusions, catatonic behavior and prominent hallucinations, and ultimately results in a profound decline in the psychosocial affect of the subject suffering therefrom. Traditionally, schizophrenia has been treated with Klonopin, which is available as a tablet containing clonezepam, available from Hoffmann-LaRoche Inc.; Thorazine, which is available as a tablet containing chlorpromazine, available from SmithKline Beecham Pharmaceuticals; and Clozaril, which is a tablet containing clozapine, available from Sandoz Pharmaceuticals. Such neuroleptics are believed to be effective as a result of interaction thereof with the dopaminergic pathways of the CNS. In addition, a dopaminergic dysfunction possessed by individuals suffering from schizophrenia has been proposed. See, Lieberman et al., *Schizophr. Bull.*, Vol. 19, pp. 371–429 (1993) and Glassman, *Amer. J. Psychiatry.*, Vol. 150, pp. 546–553 (1993). Nicotine has been proposed as being effective in effecting neurotransmitter dysfunction associated with schizophrenia. See, Merriam et al., *Psychiatr. Annals*, Vol. 23, pp. 171–178 (1993) and Adler et al., *Biol. Psychiatry*, Vol. 32, pp. 607–616 (1992).

Nicotine has been proposed to have a number of pharmacological effects. Certain of those effects may be related to effects upon neurotransmitter release. See, for example, Sjak-shie et al., *Brain Res.*, Vol. 624, pp. 295–298 (1993), where neuroprotective effects of nicotine are proposed. Release of acetylcholine and dopamine by neurons upon administration of nicotine has been reported by Rowell et al., *J. Neurochem.*, Vol. 43, pp. 1593–1598 (1984); Rapier et al., J. Neurochem., Vol. 50, pp. 1123–1130 (1988); Sandor et al., *Brain Res.*, Vol. 567, pp. 313–316 (1991) and Vizi, *Br. J. Pharmacol.*, Vol. 47, pp. 765–777 (1973). Release of norepinephrine by neurons upon administration of nicotine has been reported by Hall et al., *Biochem. Pharmacol.*, Vol. 21, pp. 1829–1838 (1972). Release of serotonin by neurons upon administration of nicotine has been reported by Hery et al., *Arch. Int, Pharmacodyn. Ther.*, Vol. 296, pp. 91–97 (1977). Release of glutamate by neurons upon administration of nicotine has been reported by Toth et al., *Neurochem Res.*, Vol. 17,pp. 265–271 (1992). Therefore, it would be desirable to provide a pharmaceutical composition containing an active ingredient having nicotinic pharmacology, which pharmaceutical composition is capable of illiciting neurotransmitter release within a subject in order to prevent or treat a neurological disorder. In addition, nicotine reportedly potentiates the pharmacological behavior of certain pharmaceutical compositions used for the treatment of certain CNS disorders. See, Sanberg et al., *Pharmacol. Biochem. & Behavior*, Vol. 46, pp. 303–307 (1993); Harsing et al.,*J. Neurochem.*, Vol. 59, pp. 48–54 (1993) and Hughes, *Proceedings from Intl. Symp. Nic.*, S40 (1994). Furthermore, various other beneficial pharmacological effects of nicotine have been proposed. See, Decina et al., *Biol. Psychiatry*, Vol. 28, pp. 502–508 (1990); Wagner et al., *Pharmacopsychiatry*, Vol. 21, pp. 301–303 (1988); Pomerleau et al., *Addictive Behaviors*, Vol. 9, p. 265 (1984); Onaivi et al., *Life Sci.*, Vol. 54(3), pp. 193–202 (1994) and Hamon, *Trends in Pharmacol, Res.*, Vol. 15, pp. 36–39.

It would be desirable to provide a useful method for the prevention and treatment of a CNS disorder by administering a nicotinic compound to a patient susceptible to or suffering from such a disorder. It would be highly beneficial to provide individuals suffering from certain CNS disorders with interruption of the symptoms of those diseases by the administration of a pharmaceutical composition which has nicotinic pharmacology and which has a beneficial effect upon the functioning of the CNS, but which does not provide any significant associated side effects (e.g., increased heart rate and blood pressure) attendant with interaction of that compound with cardiovascular sites. It would be highly desirable to provide a pharmaceutical composition incorporating a compound which interacts with nicotinic receptors which have the potential to affect the functioning of the CNS, but which does not significantly affect those receptors which have the potential to induce undesirable side effects (e.g., appreciable pressor cardiovascular effects and appreciable activity at skeletal muscle sites).

SUMMARY OF THE INVENTION

The present invention, in one aspect, relates to 2-azabicyclo[2.2.1]hept-5-ene compounds. Such compounds have a bicyclic functionality; and (i) the bridge of such functionality has a length of 1 carbon atom, (ii) the bicyclic functionality can have a C—C single bond or a C—C double bond positioned at its 5–6 position, and (iii) the nitrogen of the bicyclic functionality can possess a substituent group other than hydrogen, and (iv) the 3 position of the bicyclic functionality can possess a substituent positioned such that the compound can exist in either an endo or exo form.

The present invention, in another aspect, relates to 2-azabicyclo[2.2.2]oct-5ene compounds. Such compounds have a bicyclic functionality; and (i) the bridge of such functionality has a length 2 carbon atoms, (ii) the bicyclic functionality can have a C—C single bond or a C—C double bond positioned at its 5–6 position, and (iii) the nitrogen of the bicyclic functionality can possess a substituent group other than hydrogen, and (iv) except when a C—C single bond exists at the 5–6 position of the bicyclic functionality, the 3 position of the bicyclic functionality can possess a substituent positioned such that the compound can exist in either an endo or exo form.

The present invention relates to a method for providing prevention or treatment of a central nervous system (CNS) disorder. The method involves administering to a subject an effective amount of a compound of the present invention. The compound can be administered in a free base form or in the form of a pharmaceutically acceptable salt. The compound can be administered in the form of a racemic mixture or as an enantiomer.

The present invention, in another aspect, relates to a pharmaceutical composition comprising an effective amount of a compound of the present invention. Such a pharmaceutical composition incorporates a compound which has the capability of interacting with relevant nicotinic receptor sites of a subject, and hence has the capability of acting as a therapeutic in the prevention or treatment of a CNS disorder. The compound can have a free base form or be in the form of a pharmaceutically acceptable salt. The compound can be administered in the form of a racemic mixture or as an enantiomer.

The pharmaceutical compositions of the present invention are useful for the prevention and treatment of CNS disorders. The pharmaceutical compositions provide therapeutic benefit to individuals suffering from certain CNS disorders and exhibiting clinical manifestations of such disorders in that the compounds within those compositions have the potential to (i) exhibit nicotinic pharmacology and affect nicotinic receptors sites in the CNS (e.g., act as a pharmacological agonist to activate nicotinic receptors), and (ii) elicit neurotransmitter secretion, and hence prevent and suppress the symptoms associated with those diseases. In addition, the compounds are expected to have the potential to (i) increase the number of nicotinic cholinergic receptors of the brain of the patient, (ii) exhibit neuroprotective effects and (iii) not provide appreciable adverse side effects (e.g., significant increases in blood pressure and heart rate, and significant effects upon skeletal muscle). The pharmaceutical compositions of the present invention are believed to be safe and effective with regards to prevention and treatment of CNS disorders.

DETAILED DESCRIPTION OF THE PREFERRED EMBODIMENTS

The present invention relates to certain compounds having the formula:

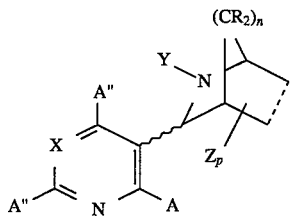

where X is nitrogen or carbon bonded to a substituent species characterized as having a sigma m value greater than 0, often greater than 0.1, generally greater than 0.2 and even greater than 0.3; less than 0 and generally less than −0.1; or 0; as determined in accordance with Hansch et al., *Chem. Rev.*, Vol. 91, pp. 165–195 (1991); n is an integer which can range from 1 to 2; R individually represents hydrogen or lower alkyl (e.g., alkyl containing one to five carbon atoms, such as methyl, ethyl or isopropyl), and preferably all R are hydrogen; Z represents lower alkyl (e.g., alkyl containing one to five carbon atoms, such as methyl, ethyl or isopropyl); A, A' and A" individually represent hydrogen, alkyl (e.g., lower straight chain or branched alkyl, including $C_1$–$C_7$, but preferably methyl or ethyl), or halo (e.g., F, Cl, Br or I), and A" can represent an aromatic group-containing species, such as aryl, phenyl, pyridyl, arylalkyl (e.g., where the alkyl substituent contains 1 to 4 carbon atoms, and an exemplary arylalkyl species is benzyl) or pyrimidyl; the dashed line in the structure represents a C—C single bond or a C—C double bond; the wavy line in the structure indicates that the compound can have a 3-endo or 3-exo form; and p is an integer ranging from 0 to 7 when the dashed line is a C—C single bond, and an integer ranging from 0 to 5 when the dashed line is a C—C double bond. Preferably, p is 0 or 1, and most preferably p is 0. Y represents hydrogen, alkyl (e.g., alkyl containing 1 to 7 carbon atoms), or an aromatic group-containing species, such as aryl, phenyl, pyridyl, arylalkyl (e.g., where the alkyl substituent contains 1 to 4 carbon atoms, and an exemplary arylalkyl species is benzyl) or pyrimidyl. Preferably Y is straight chain or branched alkyl containing 1 to about 4 carbon atoms (e.g., methyl or ethyl). X includes N, C—H, C—F, C—Cl, C—Br, C—I, C—NR'R", C—CF$_3$, C—OH, C—CN, C—SH, CSCH$_3$, C—N$_3$, C—SO$_2$CH$_3$, C—OR', C—C(=O)N R'R", C—NR'C(=O)R', C—C(=O)OR', C—OC(=O)R', C—OC(=O)NR'R", C—NR'C(=O)OR', and C—Ph, where R' and R" are individually hydrogen or lower alkyl (e.g., alkyl containing one to five carbon atoms, preferably methyl or ethyl), and Ph is an aromatic group-containing species, such as aryl, phenyl, pyridyl, arylalkyl (e.g., where the alkyl substituent contains 1 to 4 carbon rooms, and an exemplary arylalkyl species is benzyl) or pyrimidyl. When X represents a carbon atom bonded to a substituent species, that substituent species often has a sigma m value which is between about −0.3 and about 0.75, and frequently between about −0.25 and about 0.6. In addition, it is highly preferred that A is hydrogen, it is preferred that A' is hydrogen, and normally A" is hydrogen. Generally, both A and A' are hydrogen; sometimes A and A' are hydrogen, and A" is chloro, methyl or ethyl; and often A, A' and A" are all hydrogen. For certain preferred compounds, the dashed line is a C—C double bond, and Y is a substituent other than hydogen (e.g., alkyl containing 1 to 4 carbon atoms). For certain preferred compounds, the dashed line is a C—C single bond, and Y is hydrogen. Representative compounds include (±)-3-exo and (±)-3endo forms of 2-methyl-3-[3-(5-bromopyridyl)]-2-azabicyclo[2.2.1 ]hept-5-ene for which X is C—Br, A, A', A", R are H, n is 1, p is 0, Y is CH3, and the dashed line represents a C—C double bond. Other representative compounds include (±)-3-exo and (±)-3-endo forms of 2-methyl-3-[3-(6-methylpyridyl)]-2-azabicyclo [2.2.1]hept-5-ene for which X is CH, A" is CH$_3$, A, A', R are H, n is 1, p is 0, Y is CH$_3$, and the dashed line represents a C—C double bond.

Of particular interest are compounds having the formula:

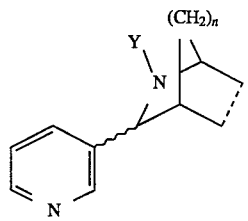

where Y, n and the dashed line are as defined hereinbefore, and those compounds can have the endo or exo form. The exo form is:

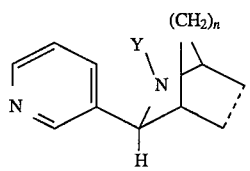

and the endo form is:

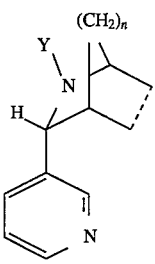

Representative compounds include (±)-3-exo and (±)-3-endo forms of 2-methyl-3(3-pyridyl)-2-azabicyclo[2.2.1]hept-5-ene, for which the dashed line is a C—C double bond, Y is —$CH_3$ and n is 1. Other representative compounds are (±)-3-exo and (±3-endo forms of 2-ethyl-3-(3-pyridyl)-2-azabicyclo[2.2.1]hept-5-ene, for which the dashed line is a C—C double bond, Y is —$CH_2$-$CH_3$ and n is 1. Other representative compounds are (±)-3-exo and (±)-3-endo forms of 2-benzyl-3-(3-pyridyl)-2azabicyclo[2.2.1]hept-5-ene, for which the dashed line is a C—C double bond, Y is —$CH_2C_6H_5$ and n is 1. Other representative compounds are (±)-3-exo and (±)-3endo forms of 2-para-anisyl-3-(3-pyridyl)-2-azabicyclo[2.2.1]hept-5-ene, for which the dashed line is a C—C double bond, Y is -$CH_2$-para-methoxyphenyl and n is 1. Other representative compounds are (±)-3-exo and (±)-3-endo forms of 3-(3-pyridyl)-2-azabicyclo[2.2.2]oct-5-ene, for which the dashed line is a C—C double bond, Y is H and n is 2. Other representative compounds are (±)-3-exo and (±)-3endo forms of 3-(3-pyridyl)-2-azabicyclo[2.2.2]oct-5-ene, for which the dashed line is a C—C double bond, Y is H and n is 2. Other representative compounds are (±)-3exo and (±)-3-endo forms of 2-methyl-3-(3-pyridyl)-2-azabicyclo[2.2.2]oct-5-ene, for which the dashed line is a C—C double bond, Y is -$CH_3$ and n is 2. Another representative compound is the racemic form of 3-(3-pyridyl)-2azabicyclo[2.2.21]octane, for which the dashed line is a C—C single bond, Y is H and n is 2. Another representative compound is the racemic form of 2-methyl-3-(3-pyridyl)-2-azabicyclo[2.2.21]octane, for which the dashed line is a C—C single bond, Y is —$CH_3$ and n is 2.

Compounds of the present invention can be synthetically produced in a step-wise fashion. Pyridyl 3-carboxaldehydes and pyrimidyl 3-carboxaldehydes are provided. Compounds such as 4-methyl-3-pyridinecarboxaldehyde, 5-methyl-3-pyridinecarboxaldehyde, 4-phenyl-3-pyridinecarboxaldehyde, 5-phenyl-3-pyridinecarboxaldehyde, 6-phenyl-3-pyridinecarboxaldehyde, 4-chloro-3-pyridinecarboxaldehyde and 5-chloro-3-pyridinecarboxaldehyde can be prepared in accordance with the types of procedures set forth in Comins et al, *Hetetrocycles*, Vol. 26, p. 2159 (1987). Compounds such a 2-methyl-3-pyridinecarboxaldehyde and 6-methyl-3-pyridinecarboxaldehyde can be provided from the corresponding substituted nicotinic acids using the types of techniques described in Swern et al, *J. Org, Chem.*, Vol. 31, p. 4226 (1966). Compounds such as 6-chloro-3-pyridinecarboxaldehyde and 6-bromo-3-pyridinecarboxaldehyde can be prepared in accordance with the techniques described by Windscheif et al, *Synthesis*, p. 87 (1994). Compounds such as 4-bromo3-pyridinecarboxaldehyde can be obtained by regiospecific lithiation of nicotinaldehyde followed by lithium/halogen exchange as reported by Kelly et al, *Tetrahedron Letters*, Vol. 34, p. 6173 (1993 ). Compounds such as 2-chloro-3pyridinecarboxaldehyde can be prepared by reduction of 2-chloro-3-cyanopyridine by Raney Nickel and formic acid as reported by Lynch et al, *Can. J. Chem.*, Vol. 66, p. 420 (1988). Compounds such as 2-bromo-3-pyridinecarboxaldehyde can be provided by direct ortho metalation of 2-bromopyridine followed by formylation with N,N-dimethyl formamide as set forth by Melnyk et al, *Synth. Commun.*, Vol. 23, p. 2727 (1993). See, also, Rondahl, L. *Acta. Pharm.*, Vol. 14, p.113 (1977).

Pyridyl 3-carboxaldehydes and pyrimidyl 3-carboxaldehydes then each are convened to the appropriate Shift base using techniques which are familiar to those skilled in the an of organic synthesis. Then, racemic mixtures of compounds of the present invention are provided by Diels Alder reaction with an appropriate cyclopentadiene.

Alternately, pyridyl 3-carboxaldehydes and pyrimidyl 3-carboxaldehydes are converted to their corresponding bis-carbamates using techniques which are familiar to those skilled in the an of organic synthesis. Then, racemic mixtures of compounds of the present invention are provided by Diels Alder reaction with an appropriate cyclohexadiene.

Compounds of the present invention can be provided as mixtures of (±)-3-exo and (±)-3-endo isomers, and the mixtures can be separated into the (±)-3-exo form and the (±)-3-endo form using column chromatography techniques. For example, (±)-exo-2-ethyl-3-(3-pyridyl)-2-azabicyclo [2.2.1]hept-5-ene is prepared from a mixture of isomers at a yield of 20% using silica gel chromatography (200–400 mesh), eluting with 5% of methanol in chloroform as eluent, and such isomer has a migration value ($R_f$) of 0.41 when analyzed by thin layer chromatography, using a solvent system of chloroform-methanol (90:10,v/v). The corresponding (±)-endo-isomer is similarly obtained using a silica gel chromatography and has $R_f$=0.62. (±)-3-Exo-2-(p-methoxybenzyl)-3-(3-pyridyl)-2-azabicyclo[2.2.1]hept-5-ene is prepared from a mixture of isomers at a yield of 14% using silica gel chromatography (200–400 mesh), eluting with 3% of methanol in chloroform as eluent, and such isomer has $R_f$=0.48 when analyzed by thin layer chromatography, using a solvent system of methanol-chloroform (5:95, (v/v). The corresponding (±)-endo-isomer is similarly obtained using silica gel chromatography and has $R_f$=0.60. (±)-3-Exo-2-benzyl-3-(3-pyridyl)-2-azabicyclo[2.2.1]hept-5-ene is prepared from a mixture of isomers at a yield of 13% using a silica gel chromatography (200–400 mesh), eluting with 5% of methanol in chloroform as eluent, and such isomer has $R_f$=0.38 when analyzed by thin layer chromatography, using a solvent system of methanol-chloroform (5:95, v/v). The corresponding (±)-endo isomer is similarly obtained using a silica gel chromatography and has $R_f$=0.52. (±)-3-Exo-2-methyl-3-[3-(5-bromopyridyl)]-2azabicyclo[2.2.1]hept-5-ene is prepared from a mixture of isomers at a yield of 23% using silica gel chromatography (200–400 mesh, 60 Å), eluting with acetonitrile in chloroform (1:6, v/v) as eluent, and such isomer has $R_f$=0.41 when analyzed by thin layer chromatography, using a solvent system of methanol-chloroform (1:6, v/v). The corresponding (±)-endo isomer is similarly obtained using a silica gel chromatography and has $R_f$=0.45.

Racemic mixtures are provided, and the compounds of the present invention can be provided as enantiomers via chromatographic separation. Enantiomeric resolution of racemic compounds can be achieved by high performance liquid chromatography using beta-cyclodextrin bonded silica gel as the chiral stationary phase based on the method developed for nicotine and nornicotine analogs. See, Armstrong et al., *Anal. Chem.*, Vol. 60, p. 2120–2127 (1988).

Representative compounds of the present invention are (±)-3-endo-2-methyl-3-[3-(6-methylpyridyl)]-2-azabicyclo [2.2.1]hept-5-ene and (±)-3-exo-2-methyl-3-[3-(6-methylpyridyl)]-2-azabicyclo[2.2.1]hept-5-ene which are prepared essentially in accordance with the following techniques. Ethyl-6-methyl-3-pyridinecarboxylate is prepared essentially in accordance with the techniques described by E. Leete et al, *Phytochemistry*, Vol.10, p. 2687 (1971) to afford 5 g (83%) of that compound. 6-Methyl-3-pyridinemethylalcohol is prepared essentially in accordance with the techniques described in Nutaitis et al, *Org. Prep. Proc. Int.*, Vol. 24, pp.143–146 (1992) to afford 2.9 g (78%) of that compound. Dimethyl sulfoxide (3.50 mL, 44 mmol) is added dropwise at −60° C., over a period of 5 min., to a solution of oxalyl chloride (2 mL, 22 mmol) in dry methylene chloride (50 mL). The reaction mixture is stirred at −60° C. for 2 min., then a solution of 6-methyl-3-pyridinemethylalcohol (2.5 g, 20.32 mmol) in dry methylene chloride (5 mL) is added over a 15 min. period and the resulting solution is stirred for 15 min. at −60° C. Triethylamine (15mL) is added and the solution is stirred for 5 additional minutes, followed by the addition of water (100 mL). The reaction mixture is allowed to warm to room temperature and extracted with chloroform (4×25 mL). The organic extracts are dried over anhydrous $Na_2SO_4$, filtered and evaporated on a rotary evaporator to give 2.5 g of a thick syrup. The pure compound, 6-methyl-3-pyridinecarboxaldehyde, (2.09, 85%) is obtained after column chromatography over silica gel (200–400 mesh) using chloroform-methanol (98:2, v/v) as eluent. A mixture of 6-methyl-3-pyridinecarboxaldehyde (2.5 g, 20.66mmol), methylamine (12 mL, 2.0M solution in tetrahydrofuran) and molecular sieves (3 Å, 5.0 g) are stirred for 12 hours under a nitrogen atmosphere. The reaction mixture is then filtered through celite. Concentration of the resulting solution on a rotary evaporator yields the Schiff base, N-[3-(6-methylpyridylidene)]methylamine, (2.6 g, 95%) which is used immediately in the next step without further purification. A solution of N-[3-(6-methylpyridylidene)]methylamine (1.8 g, 13.43 mmol) in dry methylene chloride (10 mL, fleshly distilled over $P_2O_5$) is stirred for 30 min. with powdered 3 Å molecular sieves (5 g) under nitrogen. Titanium chloride (1.46 mL, 13.43 mmol) then is added, and the resulting mixture stirred for an additional 30 min. The mixture is cooled to −78° C. (dry ice-acetone bath) before addition of a solution of freshly distilled cyclopentadiene (2.4 mL, 26.9 mmol) in dry methylene chloride (5 mL).The reaction mixture is allowed to warm to ambient temperature overnight. Chloroform (10 mL) is added to the mixture, and the solution is filtered through a bed of Celite. The filterate is evaporated to dryness and the resulting residue is dissolved by addition of a 10% aqueous solution of sodium hydroxide. The resulting solution is stirred for 10 min. and extracted with chloroform (4×10 mL). The extracts are dried over anhydrous $K_2CO_3$, filtered, and evaporated to give 2.0 g of a crude brown syrup which is shown by $^1H$ NMR to be a mixture of endo-and exo-isomers (ratio 65:35, respectively). For (±)-endo-2-methyl-3-[3-(6-methylpyridyl)]-2azabicyclo[2.2.1]hept-5-ene, $R_f$ 0.48, and the isomer is obtained by column chromatography (solvent system: methanol-chloroform (10:90, v/v)). For (±)-exo-2-methyl-3-[3-(6-methylpyridyl)]-2-azabicyclo[2.2.1]hept-5-ene, $R_f$=0.42, and the isomer is obtained by column chromatography (solvent system: methanol-chloroform (10:90, v/v)).

The present invention relates to a method for providing prevention of a CNS disorder to a subject susceptible to such a disorder, and for providing treatment to a subject suffering from a CNS disorder. In particular, the method comprises administering to a patient an amount of a compound effective for providing some degree of prevention of the progression of the CNS disorder (i.e., provide protective effects), amelioration of the symptoms of the CNS disorder, and amelioration of the reoccurrence of the CNS disorder. The method involves administering an effective amount of a compound selected from the general formulae which are set forth hereinbefore. The present invention relates to a pharmaceutical composition incorporating a compound selected from the general formulae which are set forth hereinbefore. The majority of the compounds have either an endo or exo isomeric form. The compounds can be employed as racemic mixtures or as enantiomers. The compounds can be employed in a free base form or in a salt form (e.g., as pharmaceutically acceptable salts, such as chloride, perchlorate, ascorbate, sulfate, tartrate, fumarate, citrate, malate, lactate or aspartate salts). CNS disorders which can be treated in accordance with the present invention include presenile dementia (early onset Alzheimer's disease), senile dementia (dementia of the Alzheimer's type), Parkinsonism including Parkinson's disease, Huntington's chorea, tardive dyskinesia, hyperkinesia, mania, attention deficit disorder, anxiety, dyslexia, schizophrenia and Tourette's syndrome.

The pharmaceutical composition also can include various other components as additives or adjuncts. Exemplary pharmaceutically acceptable components or adjuncts which are employed in relevant circumstances include antioxidants, free radical scavenging agents, peptides, growth factors, antibiotics, bacteriostatic agents, immunosuppressives, buffering agents, anti-inflammatory agents, anti-pyretics, time release binders, anaesthetics, steroids and corticosteroids. Such components can provide additional therapeutic benefit, act to affect the therapeutic action of the pharmaceutical composition, or act towards preventing any potential side effects which may be posed as a result of administration of the pharmaceutical composition. In certain circumstances, a compound of the present invention can be employed as part of a pharmaceutical composition with other compounds intended to prevent or treat a particular CNS disorder. As such, the pharmaceutical compositions can be formulated to provide the desired formulation.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning of the CNS.

The dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder. Thus, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the reoccurrence of the symptoms of the disorder.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount of at least about 1, often at least about 10, and frequently at least about 25 mg/ 24 hr./patient. For human patients, the effective dose of typical compounds requires administering the compound which generally does not exceed about 500, often does not exceed about 400, and frequently does not exceed about 300 mg/ 24 hr. /patient. In addition, administration of the effective dose is such that the concentration of the compound within the plasma of the patient normally does not exceed 500 ng/ml, and frequently does not exceed 100 ng/ml.

The compounds useful according to the method of the present invention have the ability to pass across the blood-brain barrier of the patient. As such, such compounds have the ability to enter the central nervous system of the patient. The log P values of typical compounds useful in carrying out the present invention generally are greater than 0, often are greater than about 1, and frequently are greater than about 1.5. The log P values of such typical compounds generally are less than about 4, often are less than about 3.5, and frequently are less than about 3. Log P values provide a measure of the ability of a compound to pass across a diffusion barrier, such as a biological membrane. See, Hansch, et al., *J. Med. Chem.*, Vol. 11, p. 1 (1968).

The compounds useful according to the method of the present invention have the ability to bind to, and in most circumstances, cause activation of nicotinic cholinergic receptors of the brain of the patient. As such, such compounds have the ability to express nicotinic pharmacology, and in particular, to act as nicotinic agonists. The receptor binding constants of preferred compounds useful in carrying out the present invention generally exceed about 1 nM, often exceed about 200 nM, and frequently exceed about 500 nM. The receptor binding constants of such preferred compounds generally are less than about 10 uM, often are less than about 7 uM, and frequently are less than about 2 uM. Receptor binding constants provide a measure of the ability of the compound to bind to half of the relevant receptor sites of certain brain cells of the patient. See, Cheng, et al., *Biochem. Pharmacol.*, Vol. 22, pp. 3099–3108 (1973).

The compounds useful according to the method of the present invention have the ability to demonstrate a nicotinic function by effectively eliciting neurotransmitter secretion from nerve ending preparations (i.e., synaptosomes). As such, such compounds have the ability to cause relevant neurons to release or secrete acetylcholine, dopamine, and other neurotransmitters. Generally, certain compounds useful in carrying out the present invention provide for the secretion of dopamine in amounts of at least about 10 percent, often at least about 20 percent, and frequently at least about 30 percent, of that elicited by an equal molar amount of S(−) nicotine.

The compounds of the present invention, when employed in effective amounts in accordance with the method of the present invention, lack the ability to elicit activation of nicotinic receptors of human muscle to any significant degree. In that regard, the compounds of the present invention demonstrate poor ability to cause isotopic rubidium ion flux through nicotinic receptors in cell preparations derived from muscle preparations. Generally, preferred compounds useful in carrying the present invention activate isotopic rubidium ion flux by less than 15 percent, often by less than 10 percent, and frequently by less than 5 percent, of that elicited by an equal molar amount of (S)–(−)-nicotine.

The compounds of the present invention, when employed in effective amounts in accordance with the method of the present invention, are selective to certain relevant nicotinic receptors, but do not cause significant activation of receptors associated with undesirable side effects. By this is meant that a particular dose of compound resulting in prevention and/or treatment of a CNS disorder, is essentially ineffective in eliciting activation of certain ganglionic-type nicotinic receptors. This selectivity of the compounds of the present invention against those receptors responsible for cardiovascular side effects is demonstrated by a lack of the ability of those compounds to activate nicotinic function of adrenal chromaffin tissue. As such, such compounds have poor ability to cause isotopic rubidium ion flux through nicotinic receptors in cell preparations derived from the adrenal gland. Generally, preferred compounds useful in carrying the present invention activate isotopic rubidium ion flux by less than 15 percent, often by less than 10 percent, and frequently by less than 5 percent, of that elicited by an equal molar amount of (S)–(−)– nicotine.

Compounds of the present invention, when employed in effective amounts in accordance with the method of the present invention, are effective towards providing some degree of prevention of the progression of CNS disorders, amelioration of the symptoms of CNS disorders, and amelioration to some degree of the reoccurrence of CNS disorders. However, such effective amounts of those compounds are not sufficient to elicit any appreciable side effects, as demonstrated by increased effects relating to the cardiovascular system, and effects to skeletal muscle. As such, administration of compounds of the present invention provides a therapeutic window in which treatment of certain CNS disorders is provided, and side effects are avoided. That is, an effective dose of a compound of the present invention is sufficient to provide the desired effects upon the CNS, but is insufficient (i.e., is not at a high enough level) to provide undesirable side effects. Preferably, effective administration of a compound of the present invention resulting in treatment of CNS disorders occurs upon administration of less than ⅕, often less than ⅒, and even less than ¹⁄₁₀₀, that amount sufficient to cause any side effects to a significant degree.

The following example is provided in order to further illustrate various embodiments of the invention but should not be construed as limiting the scope thereof. Unless otherwise noted, all parts and percentages are by weight.

EXAMPLE

Sample No. 1 is (±)-endo 3-(3-pyridyl)-2-azabicyclo [2.2.21]oct-5-ene fumarate which is prepared essentially in accordance with the following techniques.

N-N'-carboethoxy-(3-pyridyl)-diaminomethane (I)

This compound was prepared as reported by P.Quan et al., *J. Org. Chem.*, Vol. 30, pp. 269 (1965) and afforded 10 g (55%) of compound (I). Mp=163°–165° C. (±)-Endo and (±)-exo 3-(3-pyridyl)-2-carboethoxy-2-azabicyclo[2.2.2] oct-5-ene (II)

A solution of compound (I) (4.0g, 14.8 mmole), 1,3-cyclohexadiene (1.48 mL, 16.28 mmole), and boron trifluoride acetic acid complex (16.8 mL, 121.65 mmole) in glacial acetic acid (30 mL) was heated for 3 hours at 70° C. A solution of 40% (w/v) of NaOH in water was added to the reaction mixture, which was then extracted with chloroform (4×25 mL). The combined extracts were dried over anhydrous $K_2CO_3$, filtered and concentrated on a rotary evaporator. The resulting thick syrup was purified by column chromatography over silica gel (200–400 mesh) using acetonitrile in chloroform (1:7, v/v) as eluent and afforded 2.60 g (67%) of a mixture of (±)-endo and (±)-exo isomers (ratio 60:40, respectively). This mixture was used in the next step without separation of the isomers.

$^1$H NMR of the mixture (CDCl$_3$): δ8.44 (m, 2 H), 7.46 (m, 1H), 7.21 (m, 1H), 6.36 and 6.22 (2x m, 1H), 5.62 and 5.49 (2xm, 1H), 4.1 and 3.96 (2xm, 2H), and 2.55 (3xm, 3H), 2.42 and 2.35 (2xm, 1H), 2.08 and 1.86 (2xm, 1H 1H), 1.47 (m, 1H), 1.24, 0.92 and 0.84 (3 xt, 3H).

(±)-Endo- and (±)-exo-3-(3-pyridyl)-2-azabicyclo[2,2.2]oct-5-ₑene (III)

Compound (II) (a mixture of endo and exo isomers) (1.5g, 58.13 mmol) was dissolved in a 20% (w/v) solution of NaOH in absolute ethanol (20 mL) and the mixture refluxed for 24 hours. The organic solvent was then evaporated on a rotary evaporator. The pH of the basic residue was adjusted to 9 by addition of a solution of 2N HCl in water and the aqueous mixture was extracted with ethyl acetate (4×10 mL). The organic extracts were dried over anhydrous $K_2CO_3$, concentrated, filtered and the solvent evaporated. The thick syrup obtained was chromatographed over silica gel (200–400 mesh). Both (±)-endo and (±)-exo isomers were isolated in the pure form by silica gel chromatography by eluting with 10% of methanol in chloroform.

(±)-Endo-3-(3-pyridyl)-2-azabicyclo[2.2.21]oct-5-ene (IV)

Compound (IV) with a $R_f$ value of 0.6 (solvent system chloroform:methanol (9: 1, v/v)) was isolated from silica gel column chromatography to afforded 520 mg (48%) of pure (±)-endo-isomer.

$^1$H NMR (CDCl$_3$ ): δ8.52 (d, 1H), 8.41–8.32 (m, 1H), 7.70–7.60 (m, 1H), 7.10–7.10 (m,1H), 6.01–5.90 (m, 1H), 5.60–5.50 (m, 1H), 3.62 (t, 1H), 2.80 (br s, 1H NH), 2.50–2.36 (m, 1H), 2.33–2.28 (m, 1H), 2.20–2.12 (m, 1H), 2.02–1.92 (m, 1H), 1.70 (d, 1H).

(±)-Endo-3-(3-pyridyl)-2-azabicyclo[2.2.2]oct-5-ene fumarate(V)

To a solution of compound (IV) (100 mg, 0.537 mmol) in absolute ethanol (5 mL) was added fumaric acid (124 mg, 1.068 mmol). The resulting suspension was sonicated until complete dissolution occured. The solvent was removed on a rotary evaporator to afford a colorless syrup which was crystallized from absolute ethanol to yield 179 mg (79%) of compound (V). Mp=165°–167° C.

$^1$H NMR (D2O+TSP): δ8.75 (s, 1H), 8.69 (d, 1H), 8.38 (m, 1H), 7.30 (m 1H), 6.68 (s, 4H), 5.56 (s, 2H), 4.92 (s, 1H), 4.32 (m, 1H), 3.12 (s, 1H), 2.72–2.12 (m, 1H), 2.50–2.38 (m, 2H), 2.30 (d, 1H)

Sample No. 2 is (±)-exo-3-(3-pyridyl)-2-azabicyclo [2.2.2]oct-5-ene fumarate which is prepared essentially in accordance with the following techniques.

(±)-Exo-3-(3-pyridyl)-2-azabicyclo[2.2.21]oct-5-ene (VI)

The (±)-exo-isomer $R_f$=0.45 (solvent system; chloroform-:methanol (9:1, v/v)) is isolated after column chromatography of the crude endo-exo mixture (III) over silica gel (200–400 mesh) to afford 330 mg (30%) of the isomerically pure product.

$^1$H NMR (CDCl$_3$): δ8.58 (s, 1H), 8.42 (m, 1H), 7.82–7.78 (m, 1H), 7.26–7.15 (m, 1H), 6.16–6.04 (m, 1H), 5.48–5.38 (m, 1H), 4.72 (d, 1H), 3.61 (t, 1H,), 2.72 (d, 1H,), 2.60 (s, NH), 2.20–2.00 (m, 3H), 1.50–1.40 (m, 1H).

(±)-Exo-3-(3-pyridyl)-2-azabicyclo[2.2.2]oct-5-enₑfumarate (VII)

To a solution of compound (VI) (100 mg,0.537 mmol) in absolute ethanol (5 mL) was added fumaric acid (124 mg, 1.068. mmol). The resulting suspension was sonicated until complete dissolution occured. The solvent was removed on a rotary evaporator to give a colorless syrup which was crystallized from absolute ethanol to yield 165 mg (74%) of compound (VII). Mp=167°–169° C.

$^1$H NMR (D$_2$O & TSP): δ9.00–8.50 (brs, 2H), 8.14–8.08 (dd, 1H), 7.70 (brs, 1H), 6.60 (s, 2H), 6.00–5.88 (m, 2H), 4.80 (s, 1H), 4.20 (t, 1H), 3.00–2.95 (m, 1H), 2.62–2.45 (dd, 1H), 2.40–2.21 (m, 2H), 2.20–2.16 (d, 1H).

Sample No. 3 is (±)-endo-2-methyl-3-(3-pyridyl)-2-azabicyclo[2.2.2]oct-5-ene fumarate which is prepared essentially in accordance with the following techniques.

(±)-Endo-2-methyl-3-(3-pyridyl)-2-azabicyclo[2.2.2]oct, 5-ene (VIII)

Formic acid (5 mL, 95-97 % ) and formaldehyde(0.5 mL, 37% in water) were added to (±)- endo-3-(3-pyridyl)-2-azabicyclo[2.2.2]oct-5-ene (IV) (170 mg,0. 913 mmol) and the mixture refluxed for 24 hours under nitrogen. The reaction mixture was cooled to 0° C. (ice bath), basified with a 40% (w/v) aqueous solution of NaOH (pH=9) and extracted with chloroform (4×10 mL). The combined extracts were dried over anhydrous $K_2CO_3$, filtered and concentrated. The resulting oily residue was distilled under reduced pressure (97°–98° C./0.4 mm Hg) to give 170 mg (93%) of (±)-endo-2-methyl-3-(3-pyridyl)-2-azabicyclo[2.2.2]oct-5-ene (VIII).

$^1$H NMR (CDCl$_3$): δ8.60 (d, 1H), 8.50 (dd, 1H), 7.80–7.55 (m, 1H), 7.30 7.20 (m, 1H),6.02–5.92(m, 1H), 6.34–6.28(m, 1H),3.45 (t, 1H),3.16 (s, 1H),2.42–2.40 (m, 1H), 2.38 (s, 3H), 2.30 (m, 1H), 2.28–2.12 (m, 3H), 1.62 (d, 1H).

(±)-Endo-2-methyl-3-(3-pyridyl)-2-azabicyclo[2.2.2]oct-5-ene fumarate (IX)

To a solution of compound (VIII) (100 mg, 0.54 mmol) in absolute ethanol (5 mL) was added fumaric acid (124 mg, 1.08 mmol). The resulting suspension was sonicated until complete dissolution occured. The solvent was removed on a rotary evaporator to give a colorless syrup which was crystallized from absolute ethanol to yield 190 mg (85% ) of compound (IX). Mp=143°–144° C.

$^1$H NMR (D2O+TSP): δ8.70–8.60 (m, 2H), 8.20–8.12 (m, 1H), 7.71–7.15 (m, 1H), 6.60 (s, 4H), 6.15–6.10 (m, 1H), 5.90–5.82 (m, 1H), 4.32 (s, 1H), 4.11 (t, 1H), 2.97–2.90 (m, 1H), 2.79 (s, 3H), 2.59–2.40 (m, 2H). 2.38-2.20

Sample No. 4 is (±)-Exo-2-methyl-3-(3-pyridyl)-2-azabicyclo[2.2.2]oct-5-ene fumarate which is prepared essentially in accordance with the following techniques.

(±)-Exo-2-methyl-3-(3-pyridyl)-2-azabicylo[2.2.2]oct-5-ene (X)

Formic acid (5 mL, 95–97% ) and formaldehyde(0.5 mL, 37% in water) were added to (±)-exo-3-(3-pyridyl)-2-azabicyclo[2.2.2]oct-5-ene (VI) (150 mg, 0.75 mmol) and the mixture refluxed for 24 hours under nitrogen. The reaction mixture was cooled to 0° C. (ice bath), basified with a 40% (w/v) aqueous solution of NaOH (pH=9) and extracted with chloroform (4×10 mL). The combined extracts were dried over anhydrous K$_2$CO$_3$, filtered and concentrated. The resulting oily residue was distilled under reduced pressure (107°–108° C./0.4 mm Hg) to give 145 mg (97%) of (±)-exo-2-methyl-3-(3-pyridyl)-2-azabicyclo[2.2.2]oct-5-ene (X).

(±)-Exo-2-methyl-3-(3-pyridyl)-2-azabicylo[2.2.2]oct-5-ene fumarate (XI)

To a solution of compound (X) (50rag, 0.25mmol) in absolute ethanol (5 mL) was added fumaric acid (62 mg, 0.5 mmol). The resulting suspension was sonicated until complete dissolution occured. The solvent was removed on a rotary evaporator to afford a colorless syrup which was crystallized from absolute ethanol to yield 80 mg (74%) of compound (XI). Mp=147°–148° C.

$^1$H NMR (D2O+TSP): δ8.67–8.65 (d, 1H), 8.56 (s, 1H), 8.11–8.02 (dd, 1H), 7.87–7.69 (m, 1H), 6.62 (s, 4H), 6.20–6.00 (m, 2H), 4.90–4.82 (d, 1H), 4.08–3.98 (t, 1H), 2.90 (m, 2H), 2.60–2.50 (m, 1H), 2.40–2.20 (m, 2H), 1.90–1.73 (d, 1H).

Sample No.5 is (±)-3-(3-pyridyl)-2-azabicyclo[2.2.2]octane fumarate which was prepared essentially in accordance with the following techniques.

(±)-3-(3-pyridyl)-2-carboethoxy-2-azabicyclo[2.2.2]octane (XII)

A solution of the (±)-endo and (±)-exo isomers of 3-(3-pyridyl)-2-carboethoxy-2-azabicyclo[2.2.2]oct-5-ene, compound (II), (750 mg, 2.90 mmol) in glacial acetic acid (0.5 mL) and Pd/C (10%) was shaken under a H$_2$ atmosphere in a Parr apparatus for 2 hours. The catalyst was removed by filteration over a bed of Celite and the filterate was basified by addition of a solution of 40% of NaOH in water. The aqueous basic solution was extracted with dichloromethane (4×20 mL) to give 740 mg (98%) of compound (XII).

$^1$H NMR (CDCl$_3$): δ8.48 (m, 2H), 7.60 (m. 2H), 4.78 and 4.67 (m, 1H), 4.30 (m, 1H), 4.13 and 4.10 (q, 2H), 2.19 (m, 2H), 1.90 (m, 3H), 1.63 (m, 4H,), 1.28 and 0.90 (t, 3H).

(±)-3-(3-pyridyl)-2-azabicyclo[2.2.2]octane (XIII)

(±)-3-(3-pyridyl)-2-carboethoxy-2-azabicyclo[2.2.2]octane (XII) (500 mg, 1.92 mmol) was dissolved in a solution of 20% (w/v) NaOH in absolute ethanol (10 mL) and refluxed for 24 h. The organic solvent was evaporated on a rotary evaporator. The pH of the basic residue was adjusted to 9 by addition of a solution of 2N HCl in water and was extracted with ethyl acetate (4×10 mL). The organic extracts were dried over anhydrous K$_2$CO$_3$, and concentrated. The resulting oily residue was purified by distillation under reduced pressure (108°–110° C./0.4 mm Hg) to afford 300mg (83%) of compound (XIII).

$^1$H NMR (CDCl$_3$): δ8.62–8.61 (d, 1H), 8.44–8.41 (m, 1H), 7.80–7.72 (m, 1H), 7.24–7.21 (m, 1H), 4.30 (s, 1H), 3.71–3.63 (m, 1H), 2.20 (m, 1H), 2.0–1.51 (m, 8H), 1.42 (d, 1H).

(±)-3-(3-pyridyl)-2-azabicyclo[2.2.2]octane fumarate (XIV)

To a solution of compound (XIII) (100 mg,0.531 mmol) in absolute ethanol (5 mL) was added fumaric acid (124 mg, 1.062 mmol). The resulting suspension was sonicated until complete dissolution occurred. The solvent was removed on rotary evaporator to give a colorless syrup which was crystallized from absolute ethanol to yield 156 mg (70%) of compound (XIV). Mp=180° C. (decomposition).

$^1$H NMR (D2O, TSP): δ8.80 (br s, 2H), 8.40 (d, 1H), 7.95 (s, 1H), 6.70 (s, 2H), 5.08 (s, 1H), 4.21 (s, 1H), 3.08 (s, 1H), 2.40 (m, 1H), 2.02–1.60 (m, 8H).

Sample No. 6 is (±)-2-methyl-3-(3-pyridyl)-2-azabicyclo[2.2.2]octane fumarate which was prepared essentially in accordance with the following techniques.

(±)-2-Methyl-3-(3-pyridyl)-2-azabicylo[2.2.2]octane (XV)

Formic acid (5 mL, 95–97%) and formaldehyde (0.5 mL, 37%) were added to 3(3-pyridyl)-2-azabicylo[2.2.2]octane (XIII) (170 mg) and refluxed for 24 hours under N$_2$. The reaction mixture was cooled to 0° C. (ice bath), basified by addition of a solution of 40 % w/v NaOH in water (pH=9) and extracted with chloroform (4×10 mL). The combined extracts were dried over anhydrous K$_2$CO$_3$, filtered and concentrated. The resulting oil was purified by distillation under reduced pressure (116°–118° C./0.4 mm Hg) to give 160 mg (88%) of (±)-2-methyl-3-(3-pyridyl)-2-azabicylo[2.2.2]octane (XV).

$^1$H NMR (CDCl$_3$): δ8.85 (s, 1H), 8.80–8.10 (d, 1H), 7.78–7.71 (m, 1H), 7.23–7.20 (m, 1H), 4.70 (s, 1H), 3.60 (s, 1H), 2.5 (s, 3H), 2.25 (s, 1H), 2.20–1.95 (m, 2H), 1.80–1.69 (m, 3H), 1.50–1.42 (m, 3H).

(±)-2-Methyl-3-(3-pyridyl)-2-azabicylo[2.2.2]octane fumarate (XVI)

To a solution of compound (XV) (1 20 mg, 0.495 mmol) in absolute ethanol (5 mL) was added fumaric acid (138 mg, 1.18 mmol). The resulting suspension was sonicated until complete dissolution occurred. The solvent was removed on a rotary evaporator to give a colorless syrup which was crystallized from absolute ethanol to yield 190 mg (88%) of compound (XVI). Mp=142°–143° C.

$^1$NMR (D2O+TSP): δ8.71 (s, 1H), 8.64–8.62 (m, 1H), 8.30–8.22 (d, 1H), 7.79–7.72 (m, 1H), 6.60 (s, 3H), 4.58 (s, 1H), 3.90 (s, 1H), 2.90 (s, 3H), 2.80 (s, 1H), 2.46–2.38 (m, 1H), 2.10–1.95 (d, 2H), 1.92–1.62 (m, 5H).

Sample No. 7 is (±)-endo-2-ethyl-3-(3-pyridyl)-2-azabicyclo[2.2.1]hept-5-ene which is prepared essentially in accordance with the following techniques.

N-(3-pyridylidene)-ethylamine (XVII)

A solution of 3-pyridinecarboxaldehyde (1 g, 9.3 mmol) and ethylamine (661 mg, 10.2 mmol, 70% wt in water) was stirred at room temperature for 18 h. The reaction mixture was diluted with chloroform (20 mL) and dried over anhydrous $K_2CO_3$. The solution was filtered and the solvent was evaporated to afford N-(3-pyridylidene)-ethylamine (XVII) 1.15 g (92%), which was used immediately without further purification.

$^1$H NMR (CDCl$_3$): δ8.82 (s, 1H), 8.60 (d, 1H), 8.28 (s, 1H), 8.10 (m, 1H), 7.4–7.3 (m, 1H), 3.78–3.62 (q, 2H), 1.38–1.22 (t, 3H).

(±)-Endo-2-ethyl-3-(3-pyridyl)-2-azabicyclo[2.2.1]hept-5-ene (XVIII)

A solution of N-(3-pyridylidene)-ethylamine (XVII) (1 g, 7.46 mmol) in dry methylene chloride (10 mL, freshly distilled over $P_2O_5$) was stirred for 30 min. with powdered 4 Å molecular sieves (5 g) under nitrogen. Titanium chloride (0.82 mL,7.46 mmol) was then added, and the resulting mixture stirred for an additional 30 min. The mixture was cooled to −78° C. (dry ice-acetone bath) before addition of a solution of freshly distilled cyclopentadiene (1.35 mL, 14.92 mmole) in dry methylene chloride (5 mL). The reaction mixture was allowed to warm to ambient temperature overnight. Chloroform (10 mL) was added to the mixture, and the solution was filtered through a bed of Celite. The filterate was evaporated to dryness and the resulting residue was dissolved by addition of a 10% (w/v) aqueous solution of sodium hydroxide. The resulting solution was stirred for 10 min. and extracted with chloroform (4×10 mL). The extracts were dried over anhydrous $K_2CO_3$, filtered, and evaporated to give 1.04 g of a crude brown syrup which was shown by $^1$H NMR to be a mixture of endo-and exo-isomers (ratio 70:30, respectively). The pure (±)-endo-isomer R$_f$=0.62 (solvent system: chloroform-methanol (90:10, v/v) (700mg, 47%) was obtained by column chromatography of the mixture over silica (200–400 mesh) using 5% of methanol in chloroform as eluent.

$^1$NMR (CDCl$_3$): δ8.72 (d,1H), 8.78–8.62 (dd, 1H), 7.88–7.82 (m, 1H), 7.28–7.20 (m, 1H), 6.56–6.50 (m, 1H), 6.22–5.96 (m, 1H), 4.01 (d, 1H), 2.78 (s, 1H), 2.70 (s, 1H), 2.6–2.49 (m, 1H), 2.46–2.92 (m, 1H), 1.70–1.64 (d, 1H), 1.62–1.58 (d, 1H), 0.95 (t, 3H).

$^{13}$C NMR (CDCl$_3$): δ149.3,147.9, 141.3,137.1,135.2, 133.4, 123.6, 65.6, 64.5, 51.0, 48.2.42.2, 14.4.

Sample No. 8 is (±)-endo-2-(p-methoxybenzyl)-3-(3-pyridyl)-2-azabicyclo[2.2.1]hept-5-ene which is prepared essentially in accordance with the following techniques.

N-(3-pyridylidene)-p-methoxybenzylamine (XX)

The Schiff base (XX) was obtained as described for the preparation of compound (XVII) using p-methoxybenzylamine (2.56 g, 18.69 mmol) in place of ethylamine and afforded 3.14 g (95%) of the desired compound, which was used immediately in the next step without further purification.

$^1$H NMR (CDCl$_3$) δ9.2 (s, 1H), 8.98 (d, 1H), 8.62 (s, 1H), 8.40 (d, 1H), 7.63–7.50 (m, 2H), 7.22–7.18 (d, 2H), 5.08 (s, 1H), 4.02 (s, 3H).

(±)-Endo-2-p-methoxybenzyl-3-(3-pyridyl)-2-azabicyclo[2.2.1]hept-5-ene (XXI).

A solution of N-(3-pyridylidene)-p-methoxybenzylamine (XX) (1.7g, 7.52 mmol) in dry methylene chloride (10 mL, freshly distilled over $P_2O_5$) was stirred for 30 min. with powdered 3 Å molecular sieves (5 g) under nitrogen. Titanium chloride (0.82 mL,7.50 mmol) was then added, and the resulting mixture stirred for an additional 30 min. The mixture was cooled to −78° C. (dry ice-acetone bath) before addition of a solution of freshly distilled cyclopentadiene (1.35 mL, 14.85 mmole) in dry methylene chloride (5 mL). The reaction mixture was allowed to warm to ambient temperature overnight. Chloroform (10 mL) was added to the mixture, and the solution was filtered through a bed of Celite. The filterate was evaporated to dryness and the resulting residue was dissolved by addition of a 10% aqueous solution of sodium hydroxide. The resulting solution was stirred for 10 min. and extracted with chloroform (4×10 mL). The extracts were dried over anhydrous $K_2CO_3$, filtered, and evaporated to give 1.9 g of a crude brown syrup which was shown by $^1$H NMR to be a mixture of endo-and exo-isomers (ratio 75:25, respectively). The pure (±)-endoisomer R$_f$=0.60 (solvent system: chloroform-methanol; 95:5 (v/v))(900 mg, 41%) was obtained by silica gel chromatography (200–400 mesh) using 2% of methanol in chloroform as eluent.

$^1$H NMR (CDCl$_3$): δ8.75 (d, 1H), 8.44–8.40 (dd, 1H), 7.86–7.80 (m, 1H), 7.26 (d, 2H), 7.22–7.16 (m, 1H), 6.80 (d, 2H), 6.62–6.56 (m, 1H), 6.24–6.18 (m, 1H), 3.82 (d, 1H), 3.64 (s, 2H), 3.46 (d, 1H), 3.30 (d, 1H), 2.84 (s, 1H), 2.78 (s, 1H), 1.63 (d, 1H), 1.23 (d, 1H).

$^{13}$C NMR (CDCl$_3$): δ158.2, 149.1,147.2, 139.1,137.0, 135.0, 132.2, 131.2, 130, 122.8, 113.2, 64.82, 62.91, 57.18, 55.0, 52.08, 14.2.

Sample No.9 is (±)-endo-2-benzyl-3-(3-pyridyl)-2-azabicyclo[2.2.1]hept-5ene which is prepared essentially in accordance with the following techniques.

N-(3-pyridylidene)-benzylamine (XXIII)

The procedure described for the preparation of compound (XVII) was used, replacing p-methoxybenzylamine with benzylamine, to obtain 3.26 g (98%) of N-(3-pyridylidene)-benzylamine (XXIII).

(±)-Endo-2-benzyl-3-(3-pyridyl)-2-azabicyclo[2.2.1]hept-5-ene (XXIV)

A solution of N-(3-pyridylidene)-benzylamine (XXIII) (1.0g, 5.1 retool) in dry methylene chloride (10 mL, freshly distilled over $P_2O_5$) was stirred for 30 min. with powdered 3 Å molecular sieves (5 g) under nitrogen. Titanium chloride (0.56 mL, 5.1 mmol) was then added, and the resulting mixture stirred for an additional 30 min. The mixture was cooled to −78° C. (dry ice-acetone bath) before addition of a solution of freshly distilled cyclopentadiene (0.93 mL, 10.2 mmole) in dry methylene chloride (5 mL). The reaction mixture was allowed to warm to ambient temperature overnight. Chloroform (10 mL) was added to the mixture, and the solution was filtered through a bed of Celite. The filterate was evaporated to dryness and the resulting residue was dissolved by addition of a 10% (w/v) aqueous solution of sodium hydroxide. The resulting solution was stirred for 10 min. and extracted with chloroform (4×10 mL). The extracts were dried over anhydrous $K_2CO_3$, filtered, and evaporated to give 840mg of a crude brown syrup which was shown by $^1$H NMR to be a mixture of endo-and exo-isomers (ratio 70:30, respectively). The pure solid (±)-endo-isomer $R_f$=0.52 (solvent system: chloroform-methanol (90:10, v/v) (520mg, 39%) was obtained by silica gel chromatography (200–400 mesh) using 5% of methanol in chloroform as eluent. Mp=49°–50° C.

$^1$H NMR δ8.72 (s, 1H), 8.48–8.42 (dd, 1H), 7.92–7.84 (m, 1H), 7.40–7.20 (m, 6H), 6.65 (t, 1H), 6.80–6.22 (m, 1H), 3.88 (s, 1H), 3.54 (d, 1H), 3.42 (d, 1H), 2.94 (s, 1H), 2.80 (s, 1H), 1.74 (d, 1H), 1.34 (d, 1H).

Sample No. 10 is (±)-endo-2-methyl-3-(3-pyridyl)-2-azabicyclo[2.2.1]hept-5ene which is prepared essentially in accordance with the following techniques.

N-(3-Pyridylidene)methylamine (XXVI)

A mixture of 3-pyridinecarboxaldehyde (2.0 g, 18.6 mmol), methylamine (12 mL, 2.0M solution in THF) and molecular sieves (3 Å, 5.0 g) were stirred for 12 hours under a nitrogen atmosphere. The reaction mixture was then filtered through celite. Concentration of the resulting solution on a rotary evaporator yielded the Schiff base XXVI (2.01 g, 90%) which was used immediately in the next step without further purification.

$^1$H NMR (CDCl$_3$): δ8.82 (s, 1H), 8.61 (d, 1H), 8.30 (s, 1H), 7.38–7.24 (m, 1H), 3.56 (s, 3H).

$^{13}$C NMR(CDCl$_3$): δ159.5, 151.2, 149.8, 134.2, 131.9, 123.5, 48.3.

(±)-Endo-2-methyl-3-(3-Pyridyl)-2-azabicyclo[2.2.1]hept-5-ene (XXVII)

A solution of N-(3-pyridylidene)-methylamine (XXVI) (2.0 g, 16.66 mmol) in dry methylene chloride (10 mL, freshly distilled over $P_2O_5$) was stirred for 30 min. with powdered 3 Å molecular sieves (5 g) under nitrogen. Titanium chloride (1.82 mL, 16.6 mmol) was then added, and the resulting mixture stirred for an additional 30 min. The mixture was cooled to −78° C. (dry ice-acetone bath) before addition of a solution of freshly distilled cyclopentadiene (3.03 mL, 33.33 mmole) in dry methylene chloride (5 mL).The reaction mixture was allowed to warm to ambient temperature overnight. Chloroform (10 mL) was added to the mixture, and the solution was filtered through a bed of Celite. The filterate was evaporated to dryness and the resulting residue was dissolved by addition of a 10% (w/v) aqueous solution of sodium hydroxide. The resulting solution was stirred for 10 min. and extracted with chloroform (4×10 mL). The extracts were dried over anhydrous $K_2CO_3$, filtered, and evaporated to give 2.5 g of a crude brown syrup which was shown by $^1$H NMR to be a mixture of endo-and exo-isomers (ratio 65:35, respectively). The pure (±)-endo-isomer $R_f$=0.51 (solvent system: chloroform-methanol (90:10, v/v) (1.52 g, 49%) was obtained by silica gel chromatography (200–400 mesh) using 5% of methanol in chloroform as eluent.

$^1$NMR (CDCl$_3$): δ8.69 (d, 1H), 8.49–8.42 (dd, 1H), 7.36–7.28 (m, 1H), 7.26–7.20 (m, 1H), 6.62–6.56 (m, 1H, 6.30–6.19 (dd, 1H), 3.92 (d, 1H), 2.80 (s, 1H), 2.64 (s, 1H), 2.42 (s, 3H), 1.76–1.70 (d, 1H), 1.40–1.34 (d, 1H)

Sample No.11 is (±)-exo-2-methyl-3-(3-pyridyl)-2-azabicyclo[2.2.1]hept-5ene which is prepared essentially in accordance with the following techniques.

(±)-Exo-2-methyl-3-(3-pyridyl)-2-azabicyclo[2.2.1]hept-5-ene (XXVIII)

The (±)-exo-isomer 650 mg (21%) $R_f$=0.42 (solvent system: methanol-chloroform (10:90, v/v)) was obtained by column chromatography of the isomeric mixture over silica (200–400 mesh) using 5% of methanol in chloroform as eluent.

$^1$NMR (CDCl$_3$): δ8.50 (d, 1H), 8.83–8.00 (dd, 1H), 7.62–7.58 (m, 1H), 7.40–7.21 (m, 1H), 6.58–6.50 (m, 1H), 5.60–5.42 (m, 1H), 3.65 (s, 1H), 3.58 (d, 1H), 3.35 (t, 1H), 2.52 (s, 3H), 2.22 (d, 1H), 1.65 (d, 1H).

Sample No. 12 is (±)-endo-2-methyl-3-[3-(5-bromopyridyl)]-2-azabicyclo[2.2.1]hept-5-ene which is prepared essentially in accordance with the following techniques.

Ethyl-5-bromo-3-pyridinecarboxylate (XXXV)

This compound was prepared essentially in accordance with the techniques described by Nutaitis et al, *Org. Prep, Proc. Int.*, Vol. 24, pp. 143–146 (1992) and afforded 9.6 g (85%) of compound (XXXV).

5-Bromo-3-pyridinemethylalcohol (XXXVI).

This compound was prepared essentially as described by Nutaitis et al, *Org, Prep. Proc. Int.*, Vol. 24, pp. 143–146 (1992) et al, and afforded 3 g (73%) of compound (XXXVI).

5-Bromo-3-pyridinecarboxaldehyde (XXXVII)

DMSO (2.50 mL, 32 mmol) was added dropwise at −60° C., over a period of 5 min., to a solution of oxalyl chloride (1.45 mL, 16 mmol) in dry methylene chloride (40 mL). The reaction mixture was stirred at −60° C. for 2 min., then a solution of 5-bromo-3-pyridinemethylalcohol (3 g, 15.9 mmol) in dry methylene chloride (5 mL) was added over a 15 min. period and the resulting solution was stirred for 15 min. at −60° C. Triethylamine (10 mL) was added and the solution was stirred for 5 additional minutes, followed by the addition of water (100 mL). The reaction mixture was allowed to warm to room temperature and extracted with chloroform (4×25 mL). The organic extracts were dried over anhydrous $Na_2SO_4$, filtered and evaporated on a rotary evaporator to give 3 g of a thick syrup. The pure compound (XXXVII) (2.5 g, 84%) was obtained after column chromatography over silica gel (200–400 mesh) using chloroform-methanol (98:2, v/v) as eluent.

$^1$NMR (CDCl$_3$): δ10.00 (s, 1H), 8.92 (s, 1H), 8.82 (s, 1H), 8.22 (s, 1H). $^{13}$C NMR (CDCl$_3$): δ189.1,155.4, 149.0, 138.2, 132.0, 122.3.

N-3-[3-(5-Bromopyridylidene)]methylamine (XXXVIII)

A mixture of 5-bromo-3-pyridinecarboxaldehyde (0.5 g, 2.69 mmol), methylamine (6 mL, 2.0M solution in THF) and molecular sieves (3 Å, 3.0 g) were stirred for 12 hours under a nitrogen atmosphere. The reaction mixture was then filtered through celite. Concentration of the resulting solution on a rotary evaporator yielded the Schiff base XXXVII (508 mg, 95%) which was used immediately in the next step without further purification.

¹H NMR (CDCl₃): δ8.78–8.62 (m, 2H), 8.23 (m, 2H), 3.58 (s, 3H).

(±)-Endo-2-methyl-3-[3-(5-bromopyridyl)]-2-azabicyclo[2.2.1]hept-5-ene (XXXIX)

A solution of N-[3-(5-bromopyridylidene)methylamine (XXXVIII) (500 mg, 2.51 mmol) in dry methylene chloride (5 mL, freshly distilled over P₂O₅) was stirred for 30 min. with powdered 3 Å molecular sieves (3 g) under nitrogen. Titanium chloride (0.28 mL, 2.5 mmol) was then added, and the resulting mixture stirred for an additional 30 min. The mixture was cooled to −78° C. (dry ice-acetone bath) before addition of a solution of freshly distilled cyclopentadiene (0.45 mL, 5.02 mmol) in dry methylene chloride (3 mL). The reaction mixture was allowed to warm to ambient temperature overnight. Chloroform (10 mL) was added to the mixture, and the solution was filtered through a bed of Celite. The filterate was evaporated to dryness and the resulting residue was dissolved by addition of a 10% aqueous solution of sodium hydroxide. The resulting solution was stirred for 10 min. and extracted with chloroform (4×10 mL). The extracts were dried over anhydrous K₂CO₃, filtered, and evaporated to give 0.6 g of a crude brown syrup which was shown by ¹H NMR to be a mixture of endo-and exo-isomers (ratio 65:35, respectively). The pure (±)-endo isomer (250 mg, 37%), $R_f$=0.45 (solvent system: methanol-chloroform (1:6, v/v)) was obtained after column chromatography over silica gel (200–400 mesh, 60 Å) using acetonitrile in chloroform (1:6, v/v) as eluent.

¹H NMR (CDCl₃): δ8.49 (d, 1H), 8.15 (d, 1H), 8.70 (t, 1H), 6.50–6.43 (m, 1H), 6.16–6.11 (m, 1H), 3.81 (s, 1H), 2.70 (s, 1H), 2.54 (s, 1H), 2.14 (s, 3H), 1.61–1.55 (d, 1H), 1.30–1.25 (d, 1H).

For comparison purposes, Sample No. C-1 was provided. This sample is (S)-(−)-nicotine, which has been reported to have demonstrated a the treatment of various CNS disorders.

Determination of binding of compounds to relevant receptor sites

Rats (Sprague-Dawley) were maintained on a 12 hour light/dark cycle and were allowed free access to water and food supplied by Wayne Lab Blox, Madison, Wis. Animals used in the present studies weighed 200 to 250 g. Brain membrane preparations were obtained from brain tissue of either males or females.

Rats were killed by decapitation following anesthesia with 70% CO₂. Brains were removed and placed on an ice-cold platform. The cerebellum was removed and the remaining tissue was placed in 10 volumes (weight:volume) of ice-cold buffer (Krebs-Ringers HEPES: NaCl, 118 mM; KCl, 4.8 mM; CaCl₂, 2.5 mM; MgSO₄, 1.2 mM; HEPES, 20 mM; pH to 7.5 with NaOH) and homogenized with a glass-Teflon tissue grinder. The resulting homogenate was centrifuged at 18,000×g for 20 min. and the resulting pellet was resuspended in 20 volumes of water. After 60 min. incubation at 4° C., a new pellet was collected by centrifugation at 18,000×g for 20 min. After resuspension in 10 volumes of buffer, a new final pellet was again collected by centrifugation at 18,000×g for 20 min. Prior to each centrifugation step, the suspension was incubated at 37° C. for 5 min. to promote hydrolysis of endogenous acetylcholine. The final pellet was overlayered with buffer and stored at −70° C. On the day of the assay, that pellet was thawed, resuspended in buffer and centrifuged at 18,000×g for 20 min. The pellet obtained was resuspended in buffer to a final concentration of approximately 5 mg protein/ml. Protein was determined by the method of Lowry et al., *J. Biol. Chem.*, Vol. 193, pp. 265–275 (1951), using bovine serum albumin as the standard.

The binding of L-[³H]nicotine was measured using a modification of the method of Romano et al., *Science*, Vol. 210, pp. 647–650 (1980) as described previously by Marks et al., *Mol. Pharmacol.*, Vol. 30, pp. 427–436 (1986). The L-[³H]nicotine used in all experiments was purified chromatographically by the method of Romm, et al., *Life Sci*, Vol. 46, pp. 935–943 (1990). The binding of L-[³H]nicotine was measured using a 2 hr. incubation at 4° C. Incubations contained about 500 ug of protein and were conducted in 12 mm×75 mm polypropylene test tubes in a final incubation volume of 250 ul. The incubation buffer was Krebs-Ringers HEPES containing 200 mM TRIS buffer, pH 7.5. The binding reaction was terminated by filtration of the protein containing bound ligand onto glass fiber filters (Micro Filtration Systems) that had been soaked in buffer containing 0.5 percent polyethyleneimine. Filtration vacuum was −50 to −100 torr. Each filter was washed five times with 3 ml of ice-cold buffer. The filtration apparatus was cooled to 2° C. before use and was kept cold through the filtration process. Nonspecific binding was determined by inclusion of 10 uM nonradioactive nicotine in the incubations.

The inhibition of L-[³H]nicotine binding by test compounds was determined by including one of eight different concentrations of the test compound in the incubation. Inhibition profiles were measured using 10 nM L-[³H] nicotine and IC₅₀ values were estimated as the concentration of compound that inhibited 50 percent of specific L-[³H] nicotine binding. Inhibition constants (Ki values), reported in nM, were calculated from the IC₅₀ values using the method of Cheng et al., *Biochem Pharmacol.*, Vol. 22, pp. 3099–3108 (1973).

Determination of Dopamine Release

Dopamine release was measured by preparing synaptosomes from the striatal area of rat brain obtained from Sprague-Dawley rats generally according to the procedures set forth by Nagy et al., *J. Neurochem.*, Vol. 43, pp. 1114–1123 (1984). Striata from 4 rats were homogenized in 2 ml of 0.32M sucrose buffered with 5 mM HEPES (pH 7.5), using a glass-Teflon tissue grinder. The homogenate was diluted to 5 ml with additional homogenization solution and centrifuged at 1,000×g for 10 min. This procedure was repeated on the new pellet and the resulting supernatant was centrifuged at 12,000×g for 20 min. A 3 layer discontinuous Percoll gradient consisting of 16 percent, 10 percent and 7.5 percent Percoll in HEPES-buffered sucrose was made with the final pellet dispersed in the top layer. After centrifugation at 15,000×g for 20 min., the synaptosomes were recovered above the 16 percent layer with a Pasteur pipette, diluted with 8 ml of perfusion buffer (128 mM NaCl, 2.4 mM KCl, 3.2 mM CaCl₂, 1.2 mM KH₂PO₄, 1.2 mM MgSO₄, 25 mM HEPES pH 7.4, 10 mM dextrose, 1 mM ascorbate, 0.01 mM pargyline), and centrifuged at 15,000×g for 20 min. The new pellet was collected and re-suspended in perfusion buffer.

The synaptosome suspension was incubated for 10 min. at 37° C. [³H]-Dopamine (Amersham, 40–60 Ci/mmol) was added to the suspension to give a final concentration of 0.1 uM, and the suspension was incubated for another 5 min. Using this method, 30 to 90 percent of the dopamine was taken up into the synaptosomes, as determined by scintillation counting following filtration through glass fiber filters soaked with 0.5 percent polyethyleneimine. A continuous perfusion system was used to monitor release following exposure to each ligand. Synaptosomes were loaded onto glass fiber filters (Gelman type A/E). Perfusion buffer was dripped onto the filters (0.2–0.3 ml/min.) and pulled through the filters with a peristaltic pump. Synaptosomes were washed with perfusion buffer for a minimum of 20 min. before addition of the ligand. After the addition of 0.2 ml of a solution containing various concentrations of ligand, the perfusate was collected into scintillation vials at 1 min. intervals and the dopamine released was quantified by scintillation counting. Peaks of radioactivity released above background were summed and the average basal release during that time was subtracted from the total. Release was expressed as a percentage of release obtained with an equal concentration of (S)-(–)-nicotine.

Determination of Log P

Log P values (log octanol/water partition coefficient), which have been used to assess the relative abilities of compounds to pass across the blood-brain barrier (Hansch, et al., *J. Med. Chem.*, Vol. 11, p. 1 (1968)), were calculated according to the methods described by Hopfinger, *Conformational Properties of Macromolecules*, Academic Press (1973) using Cerius$^2$ software package by Molecular Simulations, Inc.

Determination of Interaction with Muscle

Human muscle activation was established on the human clonal line TE671/RD which is derived from an embryonal rhabdomyosarcoma (Stratton et al., *Carcinogen*, Vol. 10, pp. 899–905 (1989)). As evidenced through pharmacological (Lukas, *J. Pharmacol. Exp. Ther.*, Vol. 251, pp. 175–182 (1989)), electrophysiological (Oswald et al, *Neurosci. Lett.*, Vol. 96, pp. 207–212 (1989)), and molecular biological studies (Luther et al., *J. Neurosci.*, Vol. 9, pp. 1082–1096 (1989)) these cells express muscle-like nicotinic receptors. Nicotinic acetylcholine receptor (nAChR) function was assayed using $^{86}$Rb+ efflux according to a method described by Lukas et al., *Anal, Biochem.*, Vol. 175, pp. 212–218 (1988). The maximal activation for individual compounds (Emax) was determined as a percentage of the maximal activation induced by (S)-(–)-nicotine.

pp. 61–70 (1990)). Discussion concerning the heterogeneity of nicotinic receptors subtypes is set forth in Lukas et al., *Internatl. Review Neurobiol.*, Vol. 34, pp. 25–130 (1992). Acetylcholine nicotinic receptors expressed in rat ganglia share a very high degree of homology with their human counterparts. See, Fornasari et al., *Neurosci. Lett.*, Vol. 111, pp. 351–356 (1990) and Chini et al., *Proc. Natl. Acad, Sci. USA*, Vol. 89, pp. 1572–1576 (1992). Both clonal cell lines described above were maintained in proliferative growth phase according to routine protocols (Bencherif et al., *Mol. Cell. Neurosci.*, Vol. 2, pp. 52–65, (1991 ) and Bencherif et al., *J. Pharmacol. Exp. Ther.*, Vol. 257, pp. 946–953 (1991)). Intact cells on dishes were used for functional studies. Routinely, sample aliquots were reserved for determination of protein concentration using the method of Bradford, *Anal. Biochem.*, Vol. 72, pp. 248–254 (1976) with bovine serum albumin as the standard.

Nicotinic acetylcholine receptor (nAChR) function was assayed using $^{86}$Rb$^+$ efflux according to a method described by Lukas et al., *Anal. Biochem.*, Vol. 175, pp. 212–218 (1988). Cells were plated in 35-mm diameter wells of 6-well dishes for at least 48 hours and loaded for at least 4 hours at 37° C. in a medium containing serum, and 1 μCi/ml $^{86}$Rb$^+$. Following removal of the loading medium, cells were quickly washed three times with label-free Ringer's solution and exposed for 4 minutes at 20° C. to 900 μl of Ringer's containing the indicated concentration of compound to be tested (to define total efflux) or in addition to 100 μM mecamylamine (to define nonspecific efflux). The medium was removed and $^{86}$Rb$^+$ was quantitated using Cerenkov detection (see Lukas et al., *Anal. Biochem.*, Vol. 175, pp. 212–218 (1988)). Specific ion efflux was determined as the difference in isotope efflux between total and non-specific efflux samples. The maximal activation for individual compounds (Emax) was determined as a percentage of the maximal activation induced by (S)-(–)-nicotine.

Data are presented in Table I.

TABLE I

| Sample No. | Ki (nM) | logP | Dopamine Release | | Muscle | Ganglion |
| --- | --- | --- | --- | --- | --- | --- |
| | | | EC50 (nM) | Emax (% nicotine) | Effect (% nicotine) | Effect (% nicotine) |
| C-1* | 2 | 0.71 | 115 | 100 | 100 | 100 |
| 1 | 476 | 1.7 | 550 | 14 | 69 | 12 |
| 2 | 2 | 1.7 | 300 | 41 | 103 | 65 |
| 3 | 6359 | 1.9 | 13000 | 9 | 0 | 0 |
| 4 | 33 | 1.9 | 35000 | 17 | 8 | 8 |
| 5 | 35 | 1.9 | 2550 | 4 | 9 | 3 |
| 6 | 58 | 2.1 | 2000 | 10 | 30 | 21 |
| 7 | 7815 | 2.0 | 12900 | 22 | 18 | 2 |
| 8 | 80767 | 3.2 | >100000 | 15** | 0 | 0 |
| 9 | 141000 | 3.1 | 11000 | 30 | 7 | 11 |
| 10 | 3 | 1.4 | 86 | 44 | 25 | 18 |
| 11 | 9 | 1.5 | 90 | 58 | 7 | 55 |
| 12 | 2101 | 1.4 | 1650 | 12 | 2 | 4 |

*not an example of the invention
**Emax at 100 uM

Determination of Interaction with Ganalia

Ganglionic effects were established on the rat pheochromocytoma clonal line PC12, which is a continuous clonal cell line of neural crest origin derived from a tumor of the rat adrenal medulla expressing ganglionic-type neuronal nicotinic receptors (see Whiting et al., *Nature*, Vol. 327, pp. 515–518 (1987); Lukas, *J. Pharmacol. Exp. Ther.*, Vol. 251, pp. 175–182 (1989); Whiting et al., *Mol, Brain Res.*, Vol. 10, Sample Nos. 2, 4 and 11, which have an exo form, exhibit good high affinity binding to CNS nicotinic receptors. In addition, Sample Nos. 5 and 6, which have neither an exo nor endo form, exhibit good high affinity binding to CNS nicotinic receptors. Sample No. 10, which has an endo form, exhibits good high affinity binding to CNS nicotinic receptors. Sample Nos. 8 and 9 induce dopamine release and exhibit desirably low effects at muscle sites and ganglionic sites. Sample Nos. 4, 5, 6 and 10 exhibit good high affinity binding to CNS nicotinic receptors and exhibit desirably low effects at muscle sites and ganglionic sites.

The data in Table I indicate that the compounds have the capability of passing the blood-brain barrier by virtue of their favorable logP values. Certain compounds exhibit binding to high affinity CNS nicotinic receptors as indicated by their low binding constants. Certain compounds induce activation of CNS nicotinic receptors of a subject and cause neurotransmitter release, and thereby have the capability of demonstrating known nicotinic pharmacology. Thus, the data indicate that such compounds have the capability of being useful in treating CNS disorders involving nicotinic cholinergic systems. Furthermore, the data indicate that certain compounds do not cause any appreciable effects at muscle sites and ganglionic sites, thus indicating the potential for a lack of undesirable side effects in subjects receiving administration of those compounds.

What is claimed is:

1. A method for treating a central nervous system disorder in a patient in need thereof comprising administering to said patient an effective amount of a compound having the formula:

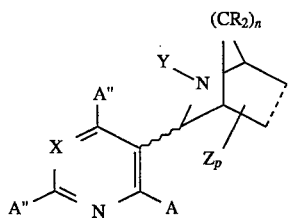

where X is nitrogen or carbon bonded to a substituent species characterized as having a sigma m value which is between about −0.3 and about 0.75; n is 2; R individually represents hydrogen or alkyl containing one to five carbon atoms; Z represents alkyl containing one to five carbon atoms; A and A' individually represent hydrogen, alkyl containing one to seven carbon atoms, or halo; A" represents hydrogen, alkyl containing one to seven carbon atoms, halo or an aromatic group-containing species; the dashed line in the structure represents a C—C double bond; the wavy line in the structure represents that the compound can have an endo or exo form; p is an integer ranging from 0 to 5; and Y represents hydrogen, alkyl containing one to seven carbon atoms or an aromatic group-containing species.

2. The method of claim 1 whereby p is 0 or 1.

3. The method of claim 1 whereby p is 0.

4. The method of claim 1 whereby R is hydrogen.

5. The method of claim 1 whereby A and A' are hydrogen.

6. The method of claim 1 whereby A and A' are hydrogen, and A" is methyl or ethyl.

7. The method of claim 1 whereby A, A' and A" are hydrogen.

8. The method of claim 1 whereby X is a member of the group consisting of N, C—H, C—F, C—Cl, C—Br, C—I, C—NR'R", C—CF$_3$, C—OH, C—CN, C—SH, C—SCH$_3$, C—N$_3$, C—SO$_2$CH$_3$, C—OR', C—C(=O)N R'R", C—NR'C(=O)R', C—C(=O)OR', C—OC(=O)R', C—OC(=O)NR'R" and C—NR'C(=O)OR', where R' and R" are individually hydrogen or alkyl containing one to five carbon atoms.

9. The method of claim 1 whereby the compound is (±)-exo-3-(3-pyridyl)-2-azabicyclo[2.2.2]oct-5-ene or (±)-endo-3-(3-pyridyl)-2-azabicyclo[2.2.2]oct-5-ene.

10. The method of claim 1 whereby the compound is (±)-exo-2-methyl-3-(3-pyridyl)-2-azabicyclo[2.2.2]oct-5-ene or (±)-endo-2-methyl-3-(3-pyridyl)-2-azabicyclo[2.2.2]oct-5-ene.

11. The method of claim 1 whereby the compound is such that the dashed line is a C—C double bond and Y is alkyl containing 1 to 4 carbon atoms.

12. The method of claim 1 wherely the central nervous system disorder is a neurodegenerative disease.

13. The method of claim 12 whereby the neurodegenerative disease is senile dementia of the Alzheimer's type.

14. The method of claim 11, whereby R is hydrogen, p is 0 and n is 2.

15. The method of claim 14, whereby A, A' and A" are hydrogen.

* * * * *